(12) United States Patent
Hogg

(10) Patent No.: US 11,367,511 B1
(45) Date of Patent: Jun. 21, 2022

(54) OPERATING DEVICES IN DIFFUSION-LIMITED FLUID REGIMES

(71) Applicant: CBN Nano Technologies Inc., Ottawa (CA)

(72) Inventor: Tad Hogg, Mountain View, CA (US)

(73) Assignee: CBN Nano Technologies Inc., Ottawa (CA)

( * ) Notice: Subject to any disclaimer, the term of this patent is extended or adjusted under 35 U.S.C. 154(b) by 327 days.

(21) Appl. No.: 16/555,379

(22) Filed: Aug. 29, 2019

Related U.S. Application Data

(60) Continuation-in-part of application No. 16/369,179, filed on Mar. 29, 2019, now abandoned, which is a division of application No. 14/319,179, filed on Jun. 30, 2014, now abandoned.

(51) Int. Cl.
*G16C 20/70* (2019.01)

(52) U.S. Cl.
CPC ................... *G16C 20/70* (2019.02)

(58) Field of Classification Search
CPC ....................................................... G16C 20/70
See application file for complete search history.

(56) References Cited

U.S. PATENT DOCUMENTS

| | | | | |
|---|---|---|---|---|
| 6,026,316 A * | 2/2000 | Kucharczyk | ........ | A61M 31/005 324/309 |
| 8,162,829 B2 * | 4/2012 | Say | ...................... | A61B 5/7455 600/365 |
| 8,743,659 B1 | 6/2014 | Hogg et al. | | |
| 8,743,660 B1 | 6/2014 | Hogg et al. | | |
| 8,755,252 B1 | 6/2014 | Hogg et al. | | |
| 8,760,972 B1 | 6/2014 | Hogg et al. | | |
| 8,787,115 B1 | 7/2014 | Hogg et al. | | |
| 8,837,258 B1 | 9/2014 | Hogg et al. | | |
| 9,063,252 B2 | 6/2015 | Kamal et al. | | |
| 10,024,950 B1 | 7/2018 | Hogg et al. | | |
| 2003/0204171 A1 * | 10/2003 | Kucharczyk | .......... | A61M 25/10 604/264 |
| 2006/0093583 A1 * | 5/2006 | Hartlep | .................. | A61B 5/055 424/93.2 |
| 2010/0268470 A1 * | 10/2010 | Kamal | .................... | E21B 47/13 702/13 |
| 2010/0286496 A1 * | 11/2010 | Simpson | ............ | A61B 5/14532 600/347 |

OTHER PUBLICATIONS

Emerbly, Eldon "Introduction to Biological Physics", Topic 8 Diffusion and Topic 9 Fluids and Swimming Low Reynolds Number (Year: 2013) (Year: 2013).*

Gurevich, Leonid Lecture 6—Diffusion and Reaction Kinetics "http://homes.nano.aau.dk/lg/PhysChem2010_files/Physical%20Chemistry2010_6.pdf" Oct. 12, 2010 (Year: 2010).*

Adriano Cavalcanti, Tad Hogg, Bijan Shirinzadeh, Hwee C. Liaw., Nanorobot Communication Techniques: 2006 9th International Conference on Control, Automation, Robotics and Vision (pp. 1-6). Dec. 1, 2006 (Year: 2006).*

(Continued)

*Primary Examiner* — Yoshihisa Ishizuka

(57) ABSTRACT

Methods are disclosed for operating devices in diffusion-limited regimes, where diffusion rates are sufficiently low that device operation can be optimized by taking the rate of diffusion into account when directing devices what actions to take.

24 Claims, 12 Drawing Sheets

(56) References Cited

OTHER PUBLICATIONS

Behkam, B. and Sitti, M.; "Bacterial Falgella-Based Propulsion and On/Off Motion Control of Microscale Objects." Applied Physics Letters, 2007, 023902, v. 90, American Institute of Physics.
Freitas Jr., R.; Nanomedicine, vol. I: Basic Capabilities, 1999, ch. 3, Landes Bioscience.
Hogg, T.; "Coordinating microscopic robots in viscous fluids", Autonomous Agents and Multi-Agent Systems, 2007, pp. 271-305, v. 14 No. 3, Kluwer Academic Publishers—Plenum Publishers.
Hogg, T. and Freitas Jr., R.; "Chemical Power for microscopic robots in capillaries", Nanomedicine: Nanotechnology, Biology and Medicine, 2010, pp. 298-317, v. 6 No. 2, Elsevier.
Martel, S. et al.; "Automatic navigation of an untethered device in the artery of a living animal using a conventional clinical magnetic resonance imaging system", Applied Physics Letters, 2007, 114105, v. 90, AIP Publishing.
Prince, J.; "Fast Diffusion in Porous Media", 2011, University of Reading, School of Mathematical and Physical Sciences.
Sakar, M.; "MicroBioRobots for Single Cell Manipulation", Publicly Accessible Penn Dissertations, 284, 2010, University of Pennsylvania.

\* cited by examiner

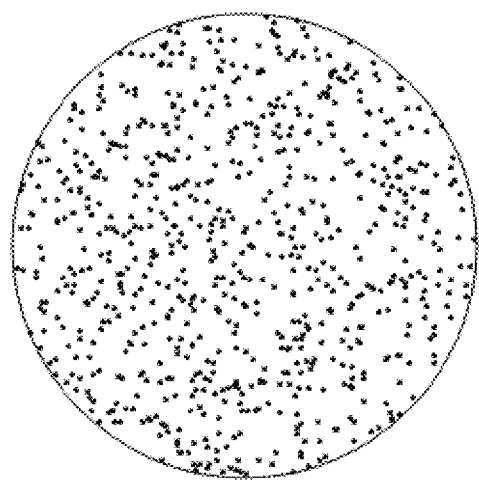
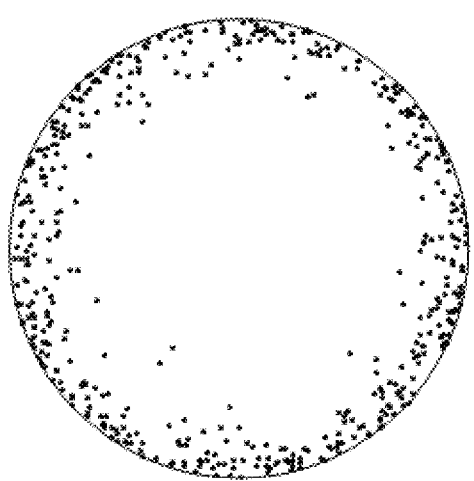
FIG. 11A          FIG. 11B
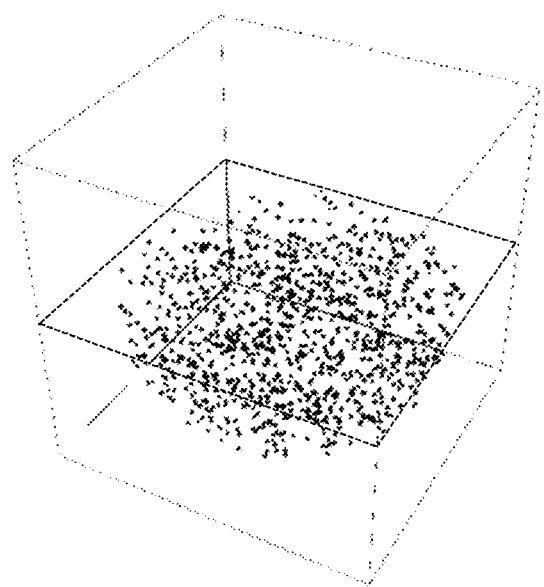
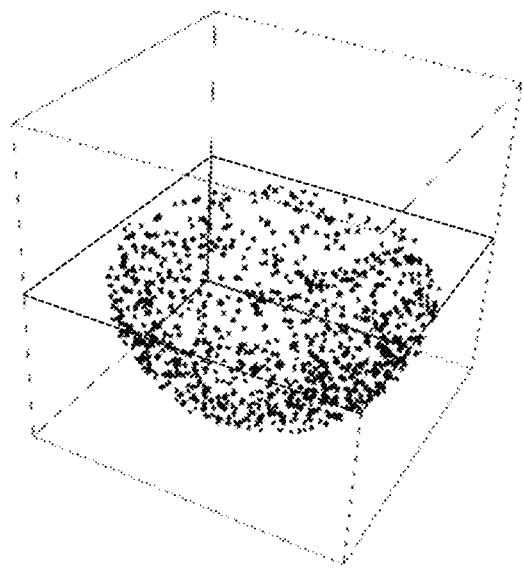
FIG. 11C          FIG. 11D

OPERATING DEVICES IN DIFFUSION-LIMITED FLUID REGIMES

CROSS-REFERENCE TO RELATED APPLICATIONS

This application is a continuation-in-part of U.S. application Ser. No. 16/369,179 filed 2019 Mar. 29, which is a division of U.S. application Ser. No. 14/319,179 filed 2014 Jun. 30, both incorporated herein by reference.

FEDERALLY SPONSORED RESEARCH

Not applicable.

SEQUENCE LISTING OR PROGRAM

Not applicable.

TECHNICAL FIELD

The invention generally relates to the effects of diffusion on devices operating in the fast diffusion regime, and more specifically how to mitigate, avoid, or correct for these effects.

BACKGROUND

Diffusion is a phenomenon that affects many organisms and devices. For example, micro-organisms will follow chemical gradients to find food. So, they are, in some sense, aware of at least one basic tenet of diffusion: Concentrations tend to be higher near the source. Even simple medical devices such as blood glucose or oxygen meters, or thermometers, are implicitly making certain assumptions about diffusion (e.g., that diffusion means that blood from, for example, your fingertip, provides an accurate representation of glucose concentrations throughout the body, or that temperature is relatively consistent throughout the body even though sampled in one location).

However, while accurate enough for some purposes, such assumptions often rest upon simplifications which do not account for fluid flow, convection, multiple sources or sinks, time-varying or location-varying concentrations, or other complicating factors. In some scenarios, and these scenarios tend to occur more frequently at smaller size scales, a much more sophisticated understanding of diffusion and the surrounding environment is required to obtain accurate data and to make informed decisions based on that data.

Herein we focus on devices operating in scenarios where the effects of diffusion can be both complex and substantial. These scenarios can occur at any size scale as long as the diffusion coefficients make some aspect of device operation diffusion-limited The Fast Diffusion Regime Diffusion is present in most environments to some degree but can often be ignored as it does not limit, for example, device operation or measurement accuracy, and diffusion is sufficient to protect the local environment from the effects of whatever is diffusing by quickly diluting it. However, when a device becomes diffusion-limited, this is no longer the case.

One way of being diffusion-limited is to be operating in the "fast diffusion regime." The fast diffusion regime is one where distances and time scales are short relative to the relevant diffusion coefficients. When a device which changes local concentrations (e.g., of chemicals, heat, electromagnetic charge, or other factors) operates in the fast diffusion regime, diffusion cannot completely offset the concentration changes. Consequently, the device alters local concentrations, and these alterations can affect both the device itself, the device's environment, and the functioning of other nearby devices.

The fast diffusion regime is not frequently encountered with typical macro-scale devices. For example, in an open environment, automobiles do not substantially deplete their surroundings of oxygen, nor cause problematic build-up of CO2, even though substantial quantities of O2 are being consumed, and substantial quantities of CO2 are being generated. This is because the diffusion coefficients for these gases are too high, the inter-device distances too large, and the flux density insufficient, to cause meaningful changes in concentration which persist for substantial times or over substantial distances. Diffusion (along with other processes depending on the scenario, such as convection) almost immediately returns local concentrations to their original values. The fast diffusion regime is encountered more frequently at smaller sizes and separation distances, although the fast diffusion regime may also be encountered at relatively large sizes if diffusion coefficients are low. A substantial body of literature exists on the fast diffusion regime at small sizes. For example, previous work discusses the fast diffusion regime in static structures such as porous media, (Prince, "Fast Diffusion in Porous Media," University of Reading, School of Mathematical and Physical Sciences, 2011), in membrane exchange (Medvedev and Stuchebrukhov, "Kinetics of proton diffusion in the regimes of fast and slow exchange between the membrane surface and the bulk solution," J Math Biol, 2, 2006), in the relaxation of magnetic fields in iron oxide particles (Strijkers and Nicolay, "Handbook of Nanophysics: Nanomedicine and Nanorobotics," CRC Press, 2010), in mixing in micro-fluidics systems (Wunderlich, Nettels et al., "Taylor dispersion and the position-to-time conversion in microfluidic mixing devices," Lab on a Chip, 1, 2014), and in biological situations concerning bacterial food, waste, and gradient sensing (Dusenbery, "Living at Micro Scale: The Unexpected Physics of Being Small," Cambridge, Mass., Harvard University Press, 2009).

While diffusion-limited regimes are frequently encountered at small sizes, it should be noted that lower diffusion coefficients are encountered in viscous fluids, since diffusion coefficients are dependent on fluid viscosity. For example, the diffusion coefficient for spherical particles is defined by the Stokes-Einstein relation:

$$D = \frac{k_B T}{6\pi (eta) R} \quad \text{(Eq. 1)}$$

where the diffusion coefficient D for a particle in a free volume depends on the Boltzmann constant ($k_B$), the absolute temperature (T), the viscosity of the fluid (eta), and the hydrodynamic radius (R) of the particle. Thus, with all other factors being equal, the diffusion coefficient is inversely proportional to the fluid viscosity.

The innate diffusion coefficient of, e.g., the solute, matters also. For example, large molecules tend to have lower diffusion coefficients than small molecules. And, in the case of the diffusion of heat, different materials can have very different thermal diffusivity, which is the heat analog of a chemical diffusion coefficient. Thermal diffusivity equals kThermal/(density*Cp) where Cp is mass specific heat at constant pressure (i.e., heat capacity divided by mass), kThermal is thermal conductivity; alternatively, thermal diffusivity equals kThermal/Cp if Cp is defined as the volume specific heat (i.e., heat capacity divided by volume).

As an example of how device size relative to diffusion rate can vary in scale, so long as the situations are dynamically similar, Table 1 compares examples of fluid viscosities at room temperature (obtained from URL http://www.vp-scientific.com/Viscosity_Tables.htm), corresponding diffusion coefficients, and corresponding device sizes for a number of different fluids. It can be seen that, with respect to diffusion rate, a 10 μm diameter device operating in water is dynamically similar to a 0.5 m or larger diameter device operating in a viscous fluid such as ketchup, sour cream, or peanut butter; this size of device is well within the capabilities of being fabricated using conventional techniques such as are well known for remotely-operated submersible devices, wireless sensors, and other devices, and techniques such as MEMS/NEMS would allow the fabrication of far smaller devices

TABLE 1

| Fluid | Viscosity (cp) | Relative Diffusion Coefficient | Equivalent size relative to diffusion |
|---|---|---|---|
| Water | 1 | $D_{EXAMPLE}$ | 10 μm |
| Blood Plasma | 1.3 to 1.7 | $0.6-0.8 \cdot D_{EXAMPLE}$ | 13-17 μm |
| Olive Oil | 56 | $0.018 \cdot D_{EXAMPLE}$ | 0.56 mm |
| SAE 40 Motor Oil | 650-900 | $1.1-1.5 \cdot 10^{-3} \cdot D_{EXAMPLE}$ | 6.5-9 mm |
| Corn Syrup | 5000 | $2 \cdot 10^{-4} \cdot D_{EXAMPLE}$ | 50 mm |
| Honey | 10,000 | $10^{-4} \cdot D_{EXAMPLE}$ | 100 mm |
| Ketchup | 50,000 | $2 \cdot 10^{-5} \cdot D_{EXAMPLE}$ | 500 mm |
| Sour Cream | 100,000 | $10^{-5} \cdot D_{EXAMPLE}$ | 1 m |
| Peanut butter | 250,000 | $4 \cdot 10^{-6} \cdot D_{EXAMPLE}$ | 2.5 m |

Devices

As should be apparent from Eq. 1 and Table 1, the size of device for which diffusion rate may be a limiting factor is dependent on the viscosity and temperature of the fluid in which the device operates. Typical features of devices that operate in a fluid environment include sensors for collecting information about the fluid environment around the device, data processing capability with a memory for directing the actions of the device and for processing and storing data collected by the sensors, a power supply, communication capability (for communication while operating and/or for uploading/downloading data when outside the fluid system), and locomotive capability. While such features are typical, it should be appreciated that not all these features are necessarily found on any particular device. Some features may not be required for a particular device or device mission. Similarly, some situations may include additional components, such as sampling ports for collecting fluid or substances contained therein, storage tanks for collected substances and/or substances to be released, and manipulators or other actuators beyond those that control locomotion, etc.

Larger-scale devices (100 mm and larger, for example) can be fabricated using conventional construction techniques well known to those skilled in the art. For smaller scale devices (such as MEMS and NEMS devices), such devices and their constituent parts are manufactured in a variety of ways, including lithography and etching, micromachining, e-beam deposition, atomic layer deposition, and others. These techniques and others, including the integration of circuitry with the devices, are well known in the appropriate fields (e.g., ("Handbook of Silicon Based MEMS Materials and Technologies," Micro and Nano Technologies, William Andrew, 2010); (Ghodssi and Lin, "MEMS Materials and Processes Handbook," MEMS Reference Shelf, Springer, 2011); (Schulz, Shanov et al., "Nanotube Superfiber Materials: Changing Engineering Design," Micro and Nano Technologies, William Andrew, 2013); (Morris and Iniewski, "Nanoelectronic Device Applications Handbook," Devices, Circuits, and Systems, CRC Press, 2013); (Choudhary and Iniewski, "MEMS: Fundamental Technology and Applications," Devices, Circuits, and Systems, CRC Press, 2013); (Sharapov, Sotula et al., "Piezo-Electric Electro-Acoustic Transducers," Microtechnology and MEMS, Springer, 2013). Additionally, three dimensional printers are available which are capable of far sub-micron feature sizes (e.g., OWL Nano, sold by Old World Technologies, Virginia Beach, Va., USA; Photonic Professional GT from Nanoscribe, Germany; and the f100 aHead from FEMTOprint SA, Switzerland). Also falling under the category of small-scale devices, biorobots have been created which use, for example, flagella from micro-organisms for motile power, and which can be steered using electrical fields, light, or other means. (Sakar, "MicroBioRobots for Single Cell Manipulation," Electrical and Systems Engineering, 284, University of Pennsylvania, 2010); (Paprotny and Bergbreiter, "Small-Scale Robotics From Nano-to-Millimeter-Sized Robotic Systems and Applications," First International Workshop, microICRA 2013, Karlsruhe, Germany, Springer, 2013).

SUMMARY

Recognition and analysis of many scenarios involving devices operating in diffusion-limited fluid regimes is lacking, being mentioned in passing in some works that address extremely small-scale situations (e.g., (Freitas, "Nanomedicine, Volume I: Basic Capabilities," Landes Bioscience, 1999), § 3.2.2), but without enough detail to fully understand the possible problems, much less the solutions.

Diffusion-limited micro-scale and nano-scale devices (the literature is generally directed to static structures or molecules, not devices) have multiple characteristics which differentiate them from the existing literature for other small-scale systems in terms of problems, analysis methods, and solutions relating to diffusion. For example, devices may be mobile, relative to the environment or each other. This would not be the case with, e.g., media or membranes. Devices may also be active, using power and absorbing or releasing chemicals in a manner dissimilar from media, membranes, or static particles. And, devices may change their activity, location, or orientation over time. These factors, and others, make the problems and solutions related to the fast diffusion regime quite different, and often more complex, for devices.

Note that while we tend to focus on micro-scale examples of operations herein, with distances on the order of nanometers to microns (suitable for the typical viscosity range of biological fluids), other examples could be smaller, or larger, as long as the requirements of operating in the fast diffusion regime are met; as noted above, in viscous fluids, the relative dimensions may range up to meter size. Most examples presented herein deal with single devices, or groups of devices. However, diffusion-limited concentration changes also occur at scales smaller than a single device. For example, the surface of a device could contain multiple binding sites, influx or absorbing ports, efflux or emitting ports, sensors (e.g., for chemicals in the traditional sense of the word, pH, temperature, charge, force, magnetic fields, radiation, or other phenomena) or other features. These features could have inter-feature spacing that was quite different from the overall device dimensions. For example, a micron-scale device might have features that were spaced nanometers apart. Thus, the techniques disclosed herein also apply to arranging such features on the surface of a device or an aggregate of devices. And, as noted above, with low diffusion coefficients, these same techniques could apply to larger devices or distances when devices are operating in more viscous fluids.

Also note that while we tend to talk about devices both as the exemplary concentration changer (what might be called a "source" or "sink" in physics, depending upon the direction of change) and "changee," this need not be the case. One or more devices could affect environmental elements which may not themselves be considered devices, but which still affect acceptable operating parameters for the device. For example, with enough power being used by one or more devices, the devices could raise the local environment's temperature to a point that harms the environment. Also, in some scenarios one might consider a device itself to be the "changee" and the environment to be the changer, such as when factors external to a device change concentrations, temperatures, viscosities, diffusion coefficients, or other parameters. And, there is nothing to preclude either a device or the environment from being both a changer and changee; in fact, this may be common.

Note that it is not only the fast diffusion regime where the instant invention applies. Rather, it is the set of scenarios where some transport (be it of mass, energy, or other) is diffusion-limited or diffusion-dominated. For example, even at long time scales, depending on the environment, diffusion may play the dominant role in mass transport as compared to fluid flow, convection, or active transport. Unless otherwise required by context, use of any of the terms "fast diffusion regime," "diffusion-limited" and "diffusion-dominated" is meant to cover the concepts inherent in all three terms.

There is no exact cutoff point for saying that a given scenario is diffusion-limited. How small a role diffusion must play before the scenario is no longer considered diffusion-limited will vary depending on the requirements of the system. For example, if a device is making concentration measurements that must be very precise, and the local analyte concentration is being perturbed via diffusion by an amount that would unacceptably distort the data, then being able to account for the effects of diffusion to correct the data is necessary and we would consider this a diffusion-limited scenario, as the device could not properly function without applying the concepts described herein. On the other hand, the same device, in the same environment, simply by reducing the required accuracy of the data collected, might not need to account for diffusion-related effects. This leads to the practical definition that if diffusion-related phenomena materially affect device design, or its function in a given type of environment, or for a given purpose, the device is diffusion-limited.

The use of power, creation of waste, generation of heat, measurement of analytes, release or absorption of chemicals, and other activity, can all mean that device operation changes concentrations in the environment.

Consider a device which uses glucose for fuel (and note that fuel sources may consist of more than one chemical, for example, the use of glucose may require oxygen). This could be convenient for, for example, biological sensors or other devices which require power and where glucose is naturally present. However, one or more glucose-powered devices operating in the bloodstream could remove enough glucose from the immediate environment that other neighboring devices (or cells) might experience a significant reduction in glucose concentration.

Other biological, industrial or other examples where a device could alter local concentrations include the use of power-related substrates such as O2 or hydrocarbons, chemicals being sequestered or degraded (e.g., removal of toxins or pollutants), disposal of waste products (e.g., CO2, other oxidation products, or fermentation products), or the use of sensors which, by virtue of their binding constant and the scarcity of the analyte, significantly deplete the surrounding area of the chemical being measured. Heat can also be diffusion-limited.

While a device may affect local concentrations, extrinsic changes in concentration (or flux, such as may occur with a change in diffusion coefficient) must be considered as well. For example, blood glucose concentrations may fluctuate for reasons having nothing to do with a device. Or, a device could move into an area of different concentrations. Additionally, viscosity or temperature could each increase or decrease, affecting the diffusion coefficient and therefore the limits of the fast diffusion regime. Fluid flow velocity can also play a role, for example, by determining whether flow is viscous, laminar, or turbulent, among other effects.

Changes in concentrations can pose problems for a device's operation, data gathering, communication, or other activities, and for the environment. For example, consider a device used for sensing the concentration of an analyte. The device's own activity, or that or nearby devices, via binding some material portion of the local analyte, could perturb the local analyte concentrations, and thus complicate the collection of accurate data. In the case of gradient sensing, the actual gradient could be reversed from what the device senses in the perturbed environment, leading to completely erroneous results, and perhaps actions, such as movement in a particular direction with respect to the gradient.

For fuel or waste issues, it is possible that the device could be unable to function, lacking the ability to consume sufficient fuel, or dispose of sufficient waste. And, an excess concentration of heat could damage a device or its surroundings, as could excess charge. Of course, depending on the application, changes in concentrations that would be considered deleterious for one purpose may be desirable for another purpose. For example, a device that generated enough heat to kill cells would be considered undesirable if the device's mission was simply to report concentration values. However, if the device's job was to kill cancer cells, the heat may be useful. Consequently, terms that imply any given effect is good or bad should be taken only as exemplary.

Understanding the situations in which devices affect concentration, and to what extent, is valuable for understanding the operating envelopes of the devices in various environments, in how best to design devices, in real-time decision making, and in correction of sensor data that would otherwise measure changes caused by the operation of the devices themselves as opposed to the intended signal, among other benefits.

Depending on the situation, concentration modeling (real-time, pre-computed or a combination thereof), monitoring (e.g., to ensure device operation does not change concentrations beyond desired ranges), remediation (to restore concentrations to a required range), pre-emptive actions, other strategies, or a combination thereof, may be required for optimum device performance.

Significant changes in concentration occur mainly when one or more devices are operating in the fast diffusion regime, and with a flux that has measurable impact on the surrounding environment (which may include other devices). This is to say that the devices (or the environmental elements they affect) are close together and operate to change one or more concentrations for a sufficiently long time, and device operation exceeds some threshold flux which causes material changes in concentration.

In the above context, "sufficiently long time" means where the typical diffusion time td, for the typical distance between devices d, is $d^2/(6D)$, where D is the chemical diffusion coefficient, is short compared to operation time $t_o$, and "close together" means the distances between devices are similar in magnitude to their linear dimensions. In such cases, a concentration changed by one device affects the concentration at other devices or in the local environment. Note that the dimensions of a device may be an aggregate dimension in the case of an ensemble of devices.

Consider that diffusion in water at body temperature ranges from a few micron$^2$/s (or less) for large proteins, protein complexes, or particles, to, for example, 5400 micron$^2$/s for H2, with most substances falling in between these extremes. So, in a case where two or more devices are operating 10 microns apart from each other, in water, at body temperature, for H2, the diffusion time scale, $d^2/(6D)$, is $(100\ um)^2/(6 \times 5400\ um^2/s) = 300$ ms. For large proteins or other particles, the diffusion time scale at the 10 micron distance could be several minutes. Most chemicals and smaller proteins have diffusion coefficients that fall between those of H2 and large proteins, but depending on the separation distance, $d^2/(6D)$ could be far less than 300 ms or longer than several minutes.

Different environments may have vastly different diffusion time scales for the same substance. For example, diffusion coefficients for the same substance in gas phase can be on the order of 10,000 times faster than in liquid phase. And, diffusion coefficients can be much lower in a viscous liquid or at low temperatures. So, the foregoing examples are not meant to be representative of all time scales, distances, or device sizes which may be properly described as operating in the fast diffusion regime. Regardless of the exact diffusion time scale, devices which affect a concentration for longer than the diffusion time scale, assuming adequate flux, will significantly affect local concentrations.

Also, sources may effectively be instantaneous but still affect the environment via diffusion. Consider a device which simply breaks open, discharging a bolus of some chemical. The release is effectively instantaneous (certainly it may be faster than the diffusion time scale). However, it may still affect the environment at a given distance over a certain period of time, and so is included in our concept of diffusion-limited scenarios, or devices operating in the fast diffusion regime. The formula for calculating concentration accounts for its variation in both space and elapsed time since the release of the chemical from the source:

$$C(r,t) = (Q/(4\pi Dt)^{3/2})\exp(-r^2/4Dt) \tag{Eq. 2}$$

Where C is concentration, r is distance from source, t is time, and D is the diffusion coefficient.

Exemplary Configurations

Many different device configurations can fall within the fast diffusion regime, including single devices operating independently, or multiple devices acting in proximity, or connected, to each other. Perhaps the simplest multi-device example is just a cloud of devices which consume some substance (e.g., glucose and/or O2) during operation. Such a cloud, once the devices get close enough together, may start to deplete the chemical environment, both for devices in the cloud, and of neighboring devices. Of course, the same phenomenon also occurs in reverse and the delivery of chemicals or excretion of waste products by devices may also be diffusion-limited. Other diffusion-like phenomena can be affected as well. For example, such a cloud could pose a heat or charge issue.

A "ringset" is another example of how closely spaced devices may be required to operate as aggregate or swarm devices over long periods of time, e.g., as sensors, or as compute or communication nodes, potentially in biological environments. (Hogg, "Coordinating microscopic robots in viscous fluids," Autonomous Agents and Multi-Agent Systems, 3, Kluwer Academic Publishers-Plenum Publishers, 2007); (Hogg and Freitas, "Chemical Power for microscopic robots in capillaries," Nanomedicine: Nanotechnology, Biology and Medicine, 2, 2010) Many other configurations are possible, so the point is not the specific configuration but rather the ability to recognize when diffusion-related issues exist due to configuration, spacing, operating environments, concentrations, diffusion coefficients, and other factors, and being able to analyze a given scenario for the problems and effects described herein and then to develop device designs and operating parameters to remediate problems or take advantage of effects.

The fast diffusion regime presents problems, and opportunities, not commonly seen in macro-scale devices. Although macro-scale devices could in theory encounter such issues given low enough diffusion coefficients, diffusion coefficients are rarely low enough. And even if they were, other phenomena (e.g., fluid flow, convection) tend to dominate, making the behavior of diffusion relatively unimportant. Consequently, diffusion-related issues tend to become material at the micro-scale. But, they have not been well investigated with respect to various scenarios involving devices.

Devices operating under diffusion-limited conditions present many different challenges and opportunities. Solutions to various problems are needed, as are strategies to use fast diffusion regime effects beneficially when possible. Further, there is value in simply recognizing when fast diffusion effects are going to impact a system, even if no corrective action is taken, so that for example, sensor data can be corrected, device operating envelopes determined, or devices designed accordingly.

Exemplary problems include insufficient availability of fuel or other substrates on which a device may need to act (e.g., glucose, H2, O2, hydrocarbons), build-up of waste products (e.g., CO2, or any one of many possible reaction by-products), excess heat (which could harm devices, cells, or other aspects of the environment, but could also be adapted for beneficial effects, such as killing cancer cells), and confounding measurements through device perturbation of concentrations. These problems can be compounded when the devices are of different sizes. Herein we present solutions and strategies for dealing with each of these issues, as well as other problems which may occur when operating devices in the fast diffusion regime.

Diffusion can be important in determining chemical concentrations as distances get smaller relative to the viscosity of fluid. For devices operating in a diffusion-limited fluid regime, this means that diffusion is potentially a limiting factor in the intended operation of the device, and may impact fuel availability, waste disposal, sensor accuracy, and other functions. Various approaches are discussed herein for identifying the problems and providing solutions for mitigating diffusion-related issues involving single devices or groups of devices, and their interaction with each other or with the environment.

When devices are used in the fast diffusion regime, there are one or more chemicals of interest where the concentrations of the chemical(s) affect the desired operation of each device. In a general scheme of operation, the concentrations of the chemicals are determined, either at their initial state or current state, and the diffusion coefficients of the chemicals in the fluid are also determined. Then target values for the concentrations are determined and positions or fluxes for the devices are calculated and the devices operated accordingly such that the target values of the concentrations are reached during the operation of the devices. It should be noted that the positions, fluxes, or a combination thereof can be calculated; for example, the device can move to a location with a different concentration, or could absorb or emit a chemical to change the concentration at its present location, or do both. Additionally, such calculations could account for convection, double diffusive convection, fluid flow, Peclet number, or Taylor dispersion. The positions or fluxes can be calculated at least partially via external computational means, at least partially via internal computational means, prior to the start of operation of the device, or during operation of the device. In one situation, one or more of the chemicals is a fuel source for the device. In such a case, the target values for the fuel source can be calculated by determining the minimal fuel source flux which allows proper function of the device. Additionally, the fuel storage capacity of the devices could be accounted for. In other cases, the device could be operated in accordance with the calculated positions or fluxes, or combination thereof; and/or in accordance with anticipatory behavior. In the case of extremely small devices, the effects of Brownian motion could be minimized or compensated for during operation of the device. In some cases, the device changes the initial or current concentrations to cause a biological effect, such as the example of increasing the concentration of a toxin to kill a cancer cell. The target values for the concentrations of the chemicals could change over time, or they could remain the same as the initial or current concentrations, in which case the device is operated so as to maintain the same concentration. Where efficient operation of the device is a priority, energy costs, time costs, or a combination thereof, are considered when determining the target values for the concentrations. In some cases, communication considerations are considered when calculating positions for the one or more devices. In some cases, one or more of the calculated fluxes can be opposite in direction to one or more of the other calculated fluxes. In some cases, the calculated positions or fluxes, or combination thereof, may change over time.

When a map of the fluid environment is available, devices operating in the fast diffusion regime can be placed by collecting data on the device's current position and using the operational goals and limitations of the device (taking diffusion rate(s) into consideration) in conjunction with the map to determine a desired position to which the devices should be moved.

A system can alter the interaction of a device in its environment, where the system includes a device operating in the fast diffusion regime with respect to a chemical or chemicals in which the device is capable of affecting concentrations of the chemicals. A computational component processes diffusion-related data to calculate a change in the device's flux, duty cycle, port location, position or a combination thereof, that results in a desired change in the concentrations of the chemicals, and the device is directed to take appropriate action responsive to such calculations.

Data collected from device sensors operating in the fast diffusion regime can be corrected by collecting chemical concentration data from the device sensors, positional data about the device sensors, and flux data associated with the devices. Perturbations in the chemical concentrations are calculated where the perturbations are caused by the fluxes, and chemical concentration data is corrected by removing the perturbations.

The number, position, or flux of chemical absorbers or emitters to use on a device operating in the fast diffusion regime is determined by identifying the chemicals to be absorbed or emitted, specifying the baseline or target chemical concentrations and diffusion coefficients, specifying the desired chemical flux, and calculating the number, position, or flux of the chemical absorbers or emitters to use which result in desired chemical flux during device operation.

BRIEF DESCRIPTION OF THE DRAWINGS

These and other features, aspects, and advantages can become better understood with regard to the following description, appended claims, and accompanying drawings where:

FIGS. 11A-D are 2-dimensional plots (FIGS. 11A & 11B) and 3-dimensional plots (FIGS. 11C & 11D) of a uniform-density distribution of multiple devices throughout a spherical area (FIGS. 11A & 11C) and a preferential distribution where the density is proportional to an exponential power of the radius (FIGS. 11B & 11D); these distributions correspond to those for the concentrations shown in the graph of FIG. 10. In the 3D plots, only those points below a section plane (indicated by dashed lines) are shown.

DETAILED DESCRIPTION

Figure 1:
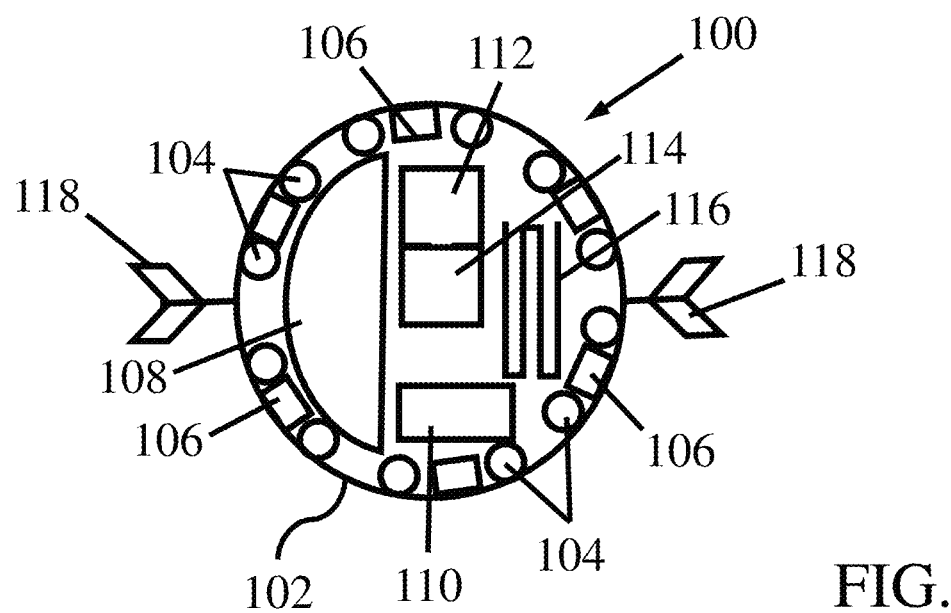
FIG. 1 is a schematic view showing one example of a device suitable for operation in a diffusion-limited fluid regime.

It should be understood that the invention is not limited to the particular systems, method, and or devices described in the following examples, as such may, of course, vary. It is also to be understood that the terminology used herein is for the purpose of describing particular embodiments only, and not intended to be limiting, since the scope of the present invention will be limited only by the appended claims.

Definitions

"Chemical," unless otherwise required by context, includes its typical meaning, and also encompasses other matter, energy or phenomena subject to diffusion.

"Concentration," unless otherwise required by context, includes its typical meaning, and also encompasses measures of other matter, energy or phenomena subject to diffusion.

"Determining," when used in the context of a device "determining" a concentration or other parameter, unless otherwise specified, can be accomplished in any manner. For example, the device could use a sensor to measure the desired quantity. Or, the device could obtain the information from another device or other device. Or, the device could have the data pre-stored in memory, in which case, "determining" could be synonymous with retrieving the data from memory. Such methods of determination could also be combined. For example, a device could store a table of diffusion coefficients associated with various temperatures, use a temperature sensor to determine the temperature, and then look up the corresponding diffusion coefficient.

"Device" is an apparatus capable of some action (unlike a static particle, membrane, or surface) such as those which may be produced by MEMS, NEMS, self-assembly, mechanosynthesis, and conventional electronics, integrated circuits, robotics, and sensor manufacture, among other techniques, which, by virtue of its size, sub-structure (e.g., ports) spacing, spacing between it and other devices or environmental elements, its interaction with the environment (e.g., concentration or gradient measurement, fuel uptake, waste disposal, payload delivery, heat generation, etc.), and the relevant diffusion coefficients, operates at least partially in the fast diffusion regime. Devices may aggregate to form other devices.

"Diffusion," unless otherwise required by context, includes diffusion of atoms, chemicals, ions, particles, objects, and diffusion-like phenomena satisfying the Diffusion Equation (which, in the special case of steady-state behavior reduces to Laplace equation), such as the diffusion of heat or electrostatic charge.

"Fast diffusion regime" is one scenario under which diffusion can be limiting due to issues such as device function, data accuracy, or environmental impact. Unless otherwise required by context, this term is interchangeable with "diffusion-limited" and "diffusion-dominated."

"Flux," unless otherwise required by context, includes changes in flux over time. A flux of zero is included.

"Port" is a device structure which allows the relative increase or decrease of some chemical in the device's environment or within the device (e.g., to load fuel tanks or sequester toxins). This may be by any means, but for example, through influx or efflux of a chemical directly, through the conversion of one chemical into another (potentially, but not necessarily, catalytically), or through the absorption or generation of heat or charge. A port with a flux of zero is still a port, as long as the possibility for non-zero flux exists. An example of a port could be an orifice connected to a pump, which is connected to a chemical storage container, and pumps out the chemical(s) as appropriate. A pump, along with many other examples described herein, could also be used in conjunction with, e.g., a semi-permeable membrane or other type of discrimination (e.g., zeolites, activated carbon, silica, etc.) method, to selectively uptake a chemical(s).

"Position" includes absolute position with respect to some reference, relative position (e.g., device to device, or device to environmental element), and orientation. Positioning in devices may be accomplished in many ways, including swimming (Behkam and Sitti, "Bacterial Flagella-Based Propulsion and On/Off Motion Control of Microscale Objects," Applied Physics Letters, 2007), molecular or DNA motors, or control by magnetic (Martel, Mathieu et al., "Automatic navigation of an untethered device in the artery of a living animal using a conventional clinical magnetic resonance imaging system," Applied Physics Letters, 2007), or electromagnetic fields (e.g., optical tweezers).

"Sensors" are devices, which may be integral to a device, distributed among multiple devices, or reside at least partially in external devices, which sense any of many different conditions or phenomena, including acceleration, acoustic waves, chemical concentrations, distance, electromagnetic radiation, physical force (including pressure, bend, stretch, torque, and others), gravity, magnetic fields, pH, subatomic particles, velocity, voltage. Not all of these phenomena are subject to diffusion, but may provide useful data in the furtherance of device operational goals.

Mathematical and Conceptual Equivalence

Various formulas and calculations are used herein. The use of these exact formulas or calculations is not the only way to perform the required computations, and therefore should be considered only exemplary. Similarly, equivalent concepts can be described using different terms. For example, one may discuss "flux" or one may discuss the product of a concentration, a diffusion coefficient and a surface area.

Additionally, some assumptions may make certain formulas, calculations or terms equivalent even if they are not in the general case. For example, when holding device surface area constant, for some purposes surface area can be ignored and changes in flux are equivalent to the change in the product of concentrations and diffusion coefficients. In the same scenario, if the diffusion coefficients are known to be static, one may equate changes in flux solely with changes in concentration, making, in some sense, flux effectively equal to concentration, even though this is not true in the general case. Equivalent formulas, terms, or obvious derivations thereof, are therefore considered part of the invention.

Subsequently we describe the analysis of several diffusion-related problems or scenarios, with an eye towards pointing out counter-intuitive phenomena (which may help recognize, or avoid, or take advantage of, other scenarios with similar underlying principles), and showing how concentration modeling can aid in informed device placement, control of flux, device design, device decision making, and other strategies that help optimize device utility. For modeling, we largely rely upon numeric and symbolic solutions analyzed by tools such as Mathematica. Other software packages, such as COMSOL, can be used for partial differential equations and finite element analysis. Such software may also have iterative solvers which will determine the best solution given a set of input parameters. Those skilled in the art will recognize the advantages and disadvantages of the various widely-available tools and techniques available for analyzing systems such as those described herein.

Flux-Limited Scenarios

Note that, while this need not be the case, for simplicity in our exemplary analyses we often assume that devices are flux-limited. Meaning, for example, if the device were absorbing a chemical, it could do so fast enough that the concentration at its surface is effectively zero. This is only an exemplary assumption. Devices can certainly be operating in the fast diffusion regime without being flux-limited, and we do present at least one analysis which forces one to consider reduced-flux scenarios (that of a cloud of devices where, if flux were not reduced, concentration in the center of the cloud would be zero).

Devices

FIG. 1 is a schematic illustration of one example of a device 100 suitable for operation in diffusion-limited scenarios. As noted herein, the size of the device for which changes in concentration of one or more chemicals of interest are diffusion-limited is at least partly dependent on the viscosity of the fluid, with high-viscosity fluids being diffusion limited at sizes in the range of 0.1-1M. The device 100 has a generally spherical body 102, with a number of ports 104 distributed across the surface, as well as a number of sensors 106 for measuring concentration. The ports 104 in this example can communicate with a storage vessel 108. The device 100 also has a power supply 110, and a data processor 112 and associated memory; the data processor 112 includes a transceiver capability and can transmit and receive data via an antenna 116. Movement of the device 100 is provided by propellers 118. Some examples of ports 104 that could be employed are shown in FIGS. 2-4.

Figure 2:
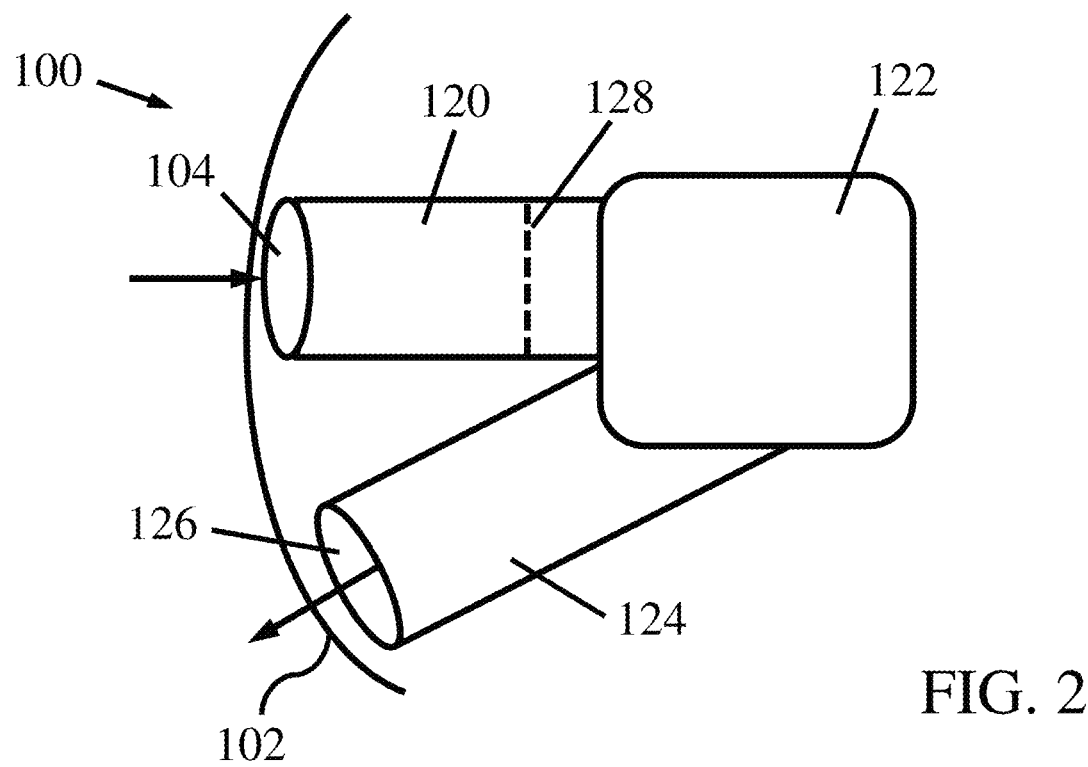
FIG. 2 is a schematic view showing one example of a port for influx of a chemical.
Figure 3:
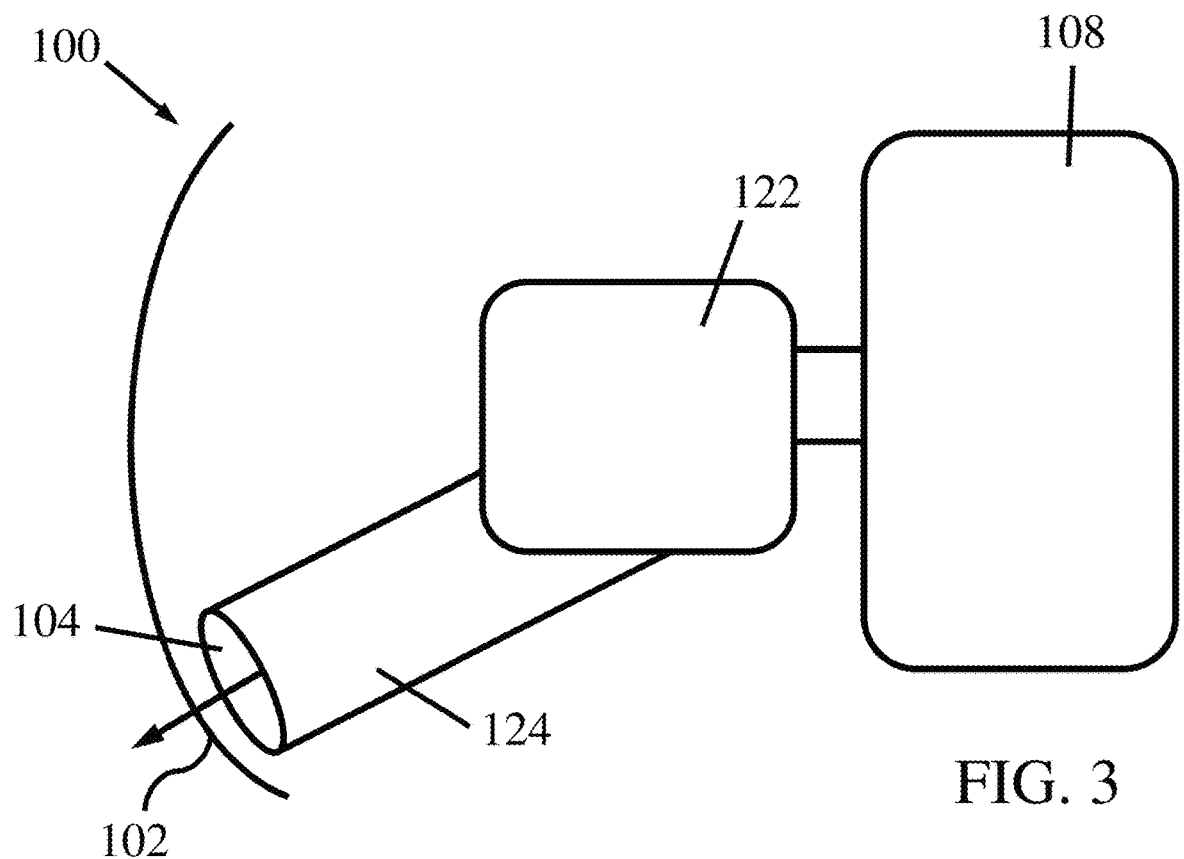
FIG. 3 is a schematic view showing one example of a port for efflux of a chemical.

FIG. 2 illustrates one example of a port 104 and related structure designed for influx of a selected chemical. The port 104 is connected via an intake duct 120 to a pump 122, which in turn ejects fluid via an output duct 124 to an exit port 126. The pump 122 moves fluid through the ducts (120, 124), such that fluid is drawn in through the port 104 and ejected from the exit port 126. A chemically-selective membrane 128 is placed in the intake duct 120, which acts to filter out a selected chemical from the fluid flow. Examples of semi-permeable and selectively-permeable membranes are well known in the art, and it should be appreciated that other structures, such as passing the fluid across chemically-selective binding sites, could be employed. Similarly, the components could be arranged to accommodate a membrane or other structure that allows the selected chemical to pass therethrough, rather than straining it out as illustrated. For example, some Zeolites are crystal structures with holes sized to fit certain molecules, and could be used to allow a chemical of interest to pass therethrough, separating it from the flow of fluid. (Jones, Tsuji et al., "Organic-functionalized molecular sieves as shape-selective catalysts," Nature, 6680, 1998; Martinez and Corma, "Inorganic molecular sieves: Preparation, modification and industrial application in catalytic processes," Coordination Chemistry Reviews, 13-14, 2011) In the example illustrated, the selected chemical is removed from the fluid flow through the ducts (120, 124), and thus the local concentration of the chemical around the device 100 is reduced. In cases where the chemical is selectively passed through, the chemical could be stored in a vessel and optionally released later under desired conditions FIG. 3 illustrates one simple example of an efflux port 104, where the output duct 124 is connected via the pump 122 to the storage vessel 108, which contains the chemical to be introduced into the local environment to increase its concentration in the vicinity of the device 100 (as noted, the stored chemical could be chemical which had previously been selectively passed through a membrane or similar structure to separate it from surrounding fluid). If the storage vessel 108 is pressurized, the pump 122 could be replaced by a valve. When it is desired to increase the concentration, the pump 122 is operated to move the stored chemical from the storage vessel 108 through the output duct 124, and out of the port 104. Small-scale pumps and valves are well-known in the art, (Zhang, Xing et al., "Micropumps, microvalves, and micromixers within PCR microfluidic chips: Advances and trends," Biotechnol Adv, 5, 2007), (Nguyen, Huang et al., "MEMS-Micropumps: A Review," Journal of Fluids Engineering, 2, 2002), (Amirouche, Zhou et al., "Current micropump technologies and their biomedical applications," Microsystem Technologies, 5, 2009) and some examples are taught in U.S. Pat. Nos. 6,955,670; 8,343,425; and 10,220,004, and U.S. Publications 2008/0161779, 2008/0202931, 2010/0284924, 2012/0015428, the teachings of which are all incorporated herein by reference. In the present application, certain U.S. patents and U.S. publications are incorporated by reference; however, the text of such U.S. patents and publications is only incorporated to the extent that no conflict exists between such text and the other statements and drawings as set forth herein. In the event of such conflict, any such conflicting material such as would be incorporated by reference by such statements herein is specifically not incorporated by reference in the present application.

Figure 4:
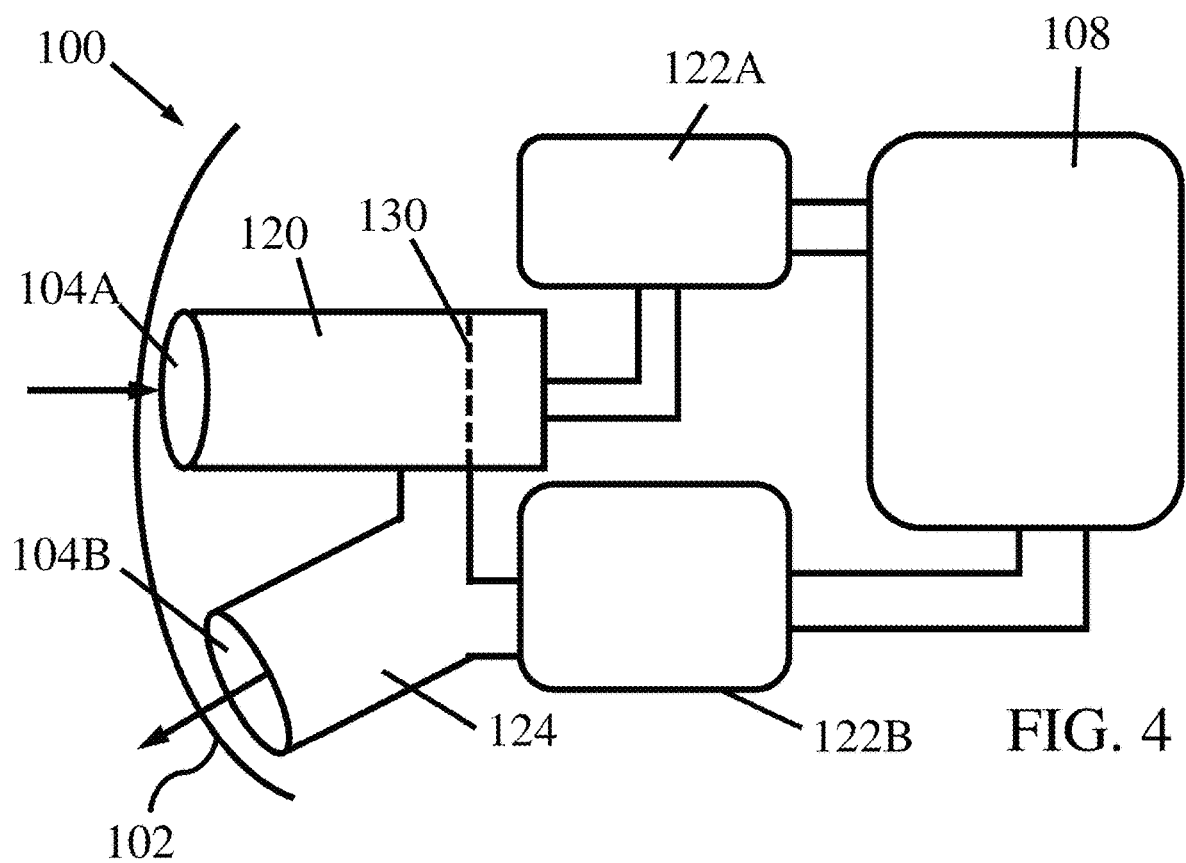
FIG. 4 is a schematic view showing one example of combined influx and efflux ports.

FIG. 4 illustrates one example of a combined influx and efflux structure, a related influx port 104A and efflux port 104B. The influx port 104A communicates with a duct 120 having a chemically-selective membrane 130; in this case, the membrane 130 is configured to selectively pass a chemical of interest, while rejecting other chemicals, and thus serves to filter out the chemical of interest, allowing it to be pumped into a storage vessel 108 via an influx pump 122A. While a chemically-selective membrane is illustrated, one skilled in the art should appreciate that other chemical-separating means such as a sorting rotor could be employed. The remaining fluid is allowed to exit via duct 124 and efflux port 104B. Since the chemical of interest is selectively removed and directed to the storage vessel 108, the local concentration is reduced when the influx pump 122A is operated. When it is desired to increase the local concentration of the chemical, efflux pump 122B can be operated to move chemical stored in the storage vessel 108 into the duct 124, from which it is released via the efflux port 104B.

Measurement Accuracy

Note that while we tend to treat concentrations as continuous quantities, in some scenarios measurements would be subject to sampling noise due to their quantized nature. For example, when measuring a rare chemical, very low concentrations may limit the accuracy with which, or minimum time period over which, a sensor can function since individual binding events will impact measurement statistics.

Concentration Effects from Single or Uniformly-Sized Devices

To more fully describe how device size relates to zones of concentration change, and more concretely define when devices are considered "close together" (which is necessarily application-dependent) consider that a sphere of radius "a" absorbing a chemical whose concentration far from the device is "C" produces a steady-state concentration profile obeying the equation:

$$C_r = C(1 - a/r) \quad \text{(Eq. 3)}$$

Where $C_r$ is the concentration at distance "r" (where r > a) from the center of a sphere of radius "a." In a flux-limited scenario, this means that at a distance of 2 times the sphere radius, the concentration is 50% of C. At a distance of 10 radii, concentration is reduced only by 10%. Therefore, depending on what concentration differences are acceptable for a given application, the definition of "close together" may vary, but this provides a way to numerically investigate solutions to the problem of devices operating close together, which will be addressed in more detail subsequently.

Note that the same concepts apply whether chemicals (including particles, heat, charge, etc.) are being emitted or absorbed. The difference is simply in the direction of the concentration change, and all exemplary scenarios herein are intended to apply to both directions, whether explicitly mentioned or not.

Concentration Effects When Device Size Differs

The simplest versions of concentration calculations involve devices of the same size. However, there is also the situation of a smaller device in proximity to a larger device. (Eq. 3) should help illustrate why this situation is potentially problematic: If the devices are the same size, and several radii apart, one device would only have minor effects on concentrations at the other devices (e.g., a 10% change at 10 radii). But, when the two devices are dissimilar in size, what is, e.g., 10 radii to the smaller device may be far less than 10 radii to the larger device.

Figure 5:
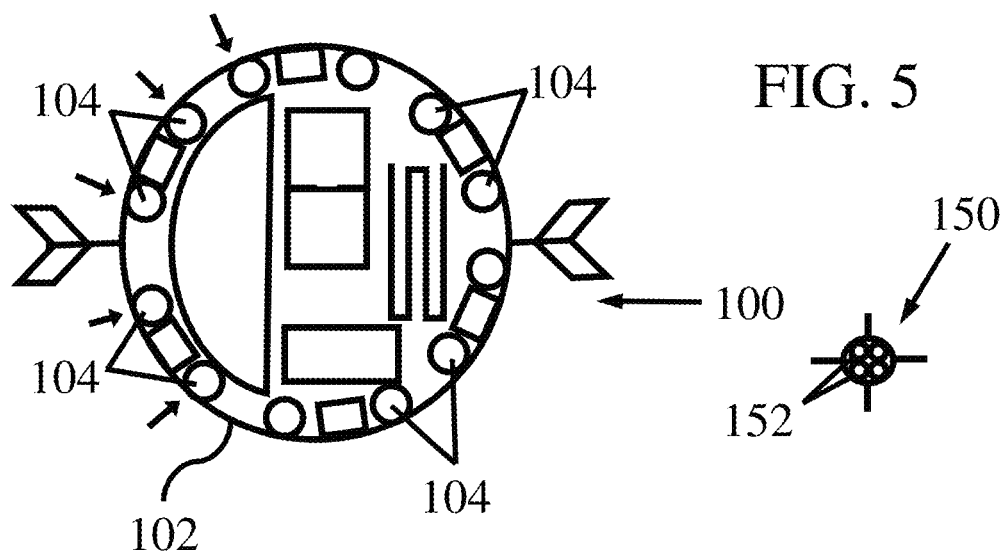
FIG. 5 illustrates the device shown in FIG. 1 operating in close proximity to a smaller device.

FIG. 5 illustrates a situation where the device 100 operates in close proximity to a much smaller device 150, having ports 152; the smaller device 150 is also generally spherical.

Consider the situation where the larger device 100 is 10 times larger than the smaller device 150. Then, from the perspective of the larger device 150, the smaller device 150 is only one radius away, not 10. In that situation, the large device 100 (assuming it is flux-limited) affects concentration at the location of the smaller device 150 by 50%. As the smaller device 150 gets even closer to the larger device 100 (for example, assume the two devices need to be in close proximity to function, or that they need to dock, or even that they just pass by each other), the smaller device 150 may pass through a region where the concentration is quite low.

Figure 6:
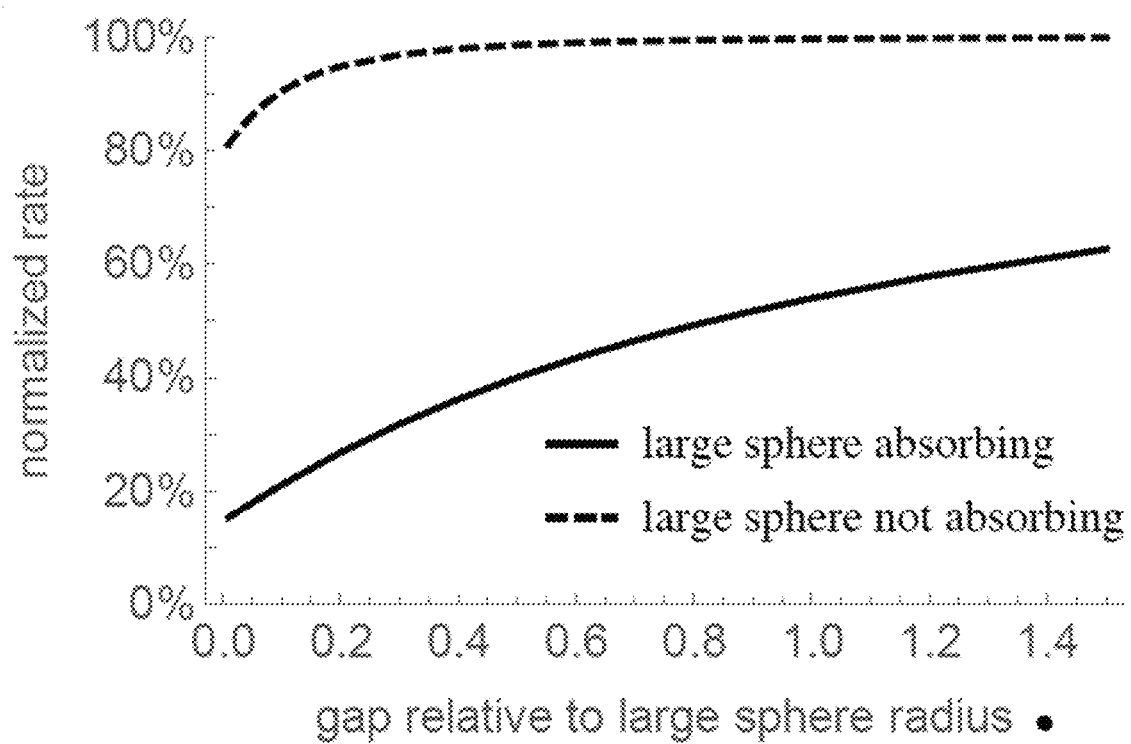
FIG. 6 is a graph showing the effect a larger device has on absorption by a smaller device at various separation distances (defined in terms of the larger sphere radius), both when the larger device is, and is not, itself absorbing.

Certainly, this may pose a problem for the smaller device 150 if the concentration of one or more chemicals become too low for the device 150 to operate properly. Solutions to this issue are discussed herein. The impact of the larger device 100 can be shown by the graph of FIG. 6, which shows 2 lines, both of which represent the rate of absorption possible by a smaller device 150 when in varying proximity to the 10× larger device 100; the proximity is shown in terms of the size of the gap between the devices (100, 150) in terms of the radius of the larger device 100, with illustrations showing the separations of the devices (100, 150) at distances of 0.2, 0.8, and 1.4 times the radius of the larger sphere 100. The bottom solid line shows the absorption rate of the smaller sphere 150 when the large sphere 100 is also absorbing, while the top dashed line illustrates the absorption rate of the smaller sphere 150 when the larger sphere is not absorbing. Note that, even when not absorbing, proximity of the larger sphere 100 causes some decrease in the absorption rate of the smaller sphere 150 simply by virtue of impeding diffusion in the volume of fluid occupied by the larger sphere 100.

Concentration Changes May be Anisotropic

A non-homogenous environment may make concentration changes vary not only with distance but also direction. For example, consider diffusion within a biological membrane of a lipid-soluble chemical. Diffusion will tend to proceed in the plane of the membrane, with potentially little or no diffusion into the aqueous media surrounding the membrane. In addition to solubility differences, such effects may be caused by physical structure. For example, consider muscle fibers, which have a high aspect ratio and are bunched together. Such an environment may have a different diffusion rate across fibers versus along fibers. Such effects may be accounted for when modeling various scenarios, as may other complexities which are discussed herein, or would be known to those skilled in the arts.

Solutions

Many diffusion-based effects have been described herein, some beneficial, some problematic, and some are perhaps neither but which preferably would be accounted for during device operation (e.g., to maximize sensor accuracy). And, formulas and methods for mathematically analyzing diffusion-based effects have been discussed (and are additionally discussed subsequently). Now we turn to strategic solutions to various problems, since, although the mathematical analyses can help numerically define diffusion-related effects in a given scenario, such analyses do not specify how to optimize device design or behavior.

Figure 7:
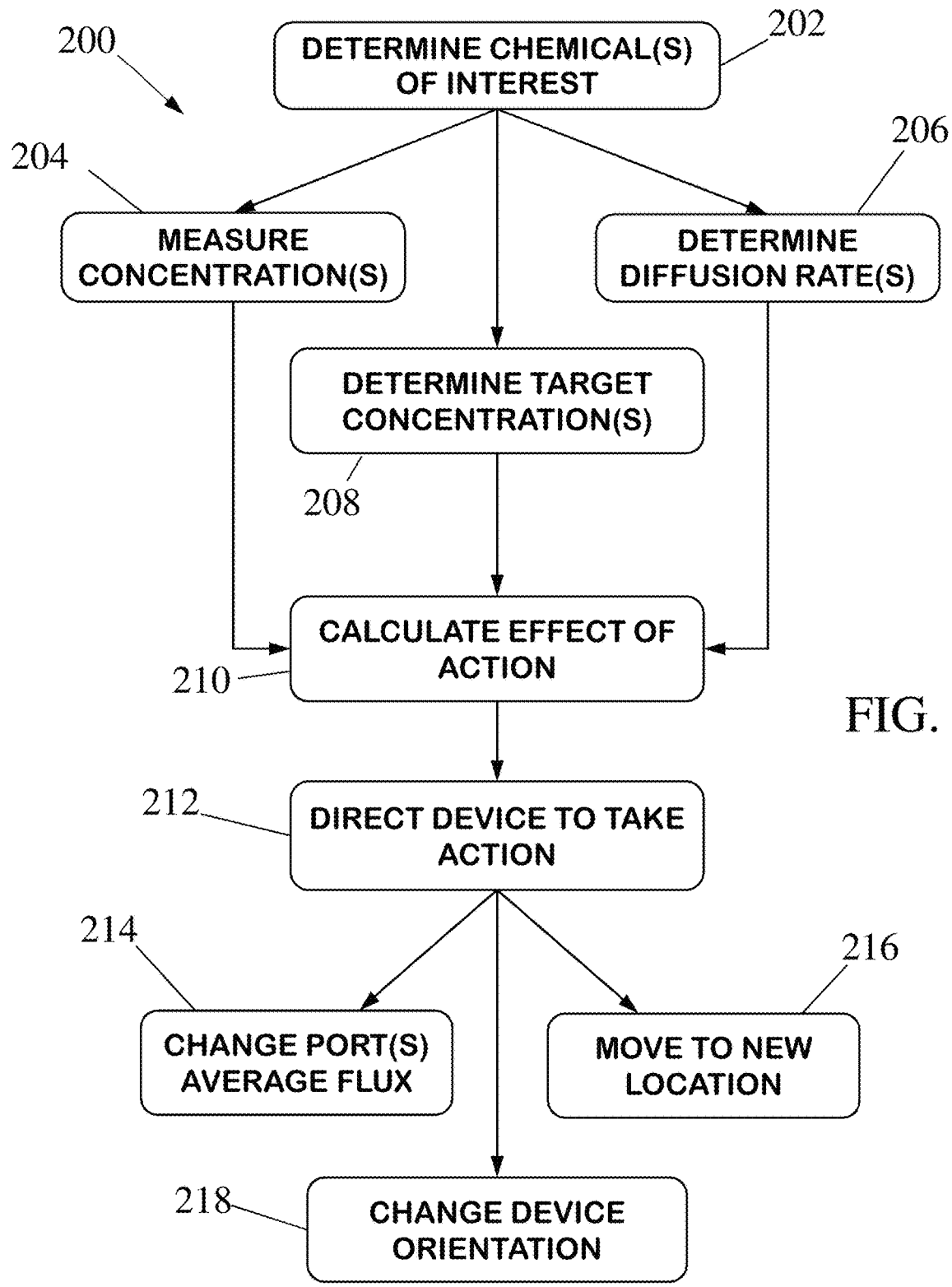
FIG. 7 is a flow chart illustrating a method for operating a device to change the concentration of one or more chemicals of interest in the local environment of the device to achieve a target concentration.

FIG. 7 illustrates a general method 200 for operating a device so as to attain a desired target concentration of one or more chemicals of interest in the local environment of the device. First, the chemical or chemicals of interest are determined 202. Such chemicals are typically those for which the proper operation of the device is dependent on concentration. Examples could include chemicals taken in for use as fuel to power the device, chemicals being measured by the device for diagnostic purposes, other chemicals to be absorbed by the device, waste products generated by the device, stored chemicals being released by the device, etc. Using one or more sensors (typically sensors on the device, but in some cases external sensing may be practical, the concentration of each chemical of interest is measured 204. The diffusion rate of each chemical is also determined 206. Where the diffusion rate throughout the range of operation of the device is expected to be relatively constant, a single global rate can be calculated based on the fluid viscosity and temperature. However, in situations where changes in the diffusion rate are expected, the rate can be periodically calculated based on current sensor measurements, such as by measuring fluid temperature and/or viscosity changes. The target concentration for each chemical is also determined 208, based on the concentration desired for proper operation of the device.

With the current measured concentration 204, the diffusion rate 206, and the target concentration 208, a calculation is performed 210 to determine how an action of the device would affect the concentration in its local environment. This calculation 210 can include determining whether the target concentration can be achieved by performing the action. For example, the calculation 210 could determine that changing the flux of ports of the device would not meet the target concentration, but that moving the device to a new location (such as after depleting the current location of the chemical) likely would be sufficient. Alternatively, the calculation 210 could compare the energy requirements of alternative schemes, to identify which action(s) can achieve the target concentration most efficiently and/or most quickly. Responsive to the calculation 210, the device is directed to take action 212. Possible actions are discussed herein in greater detail, with three options illustrated in FIG. 7; it should be appreciated that multiple actions could be combined, with some examples being discussed herein. One option is to change the average flux 214 of one or more ports; this change can be accomplished by changing the power of operation of the port(s) and/or by changing duty cycle. Another option, when the device has locomotive capability, is to move to a new location 216. Note that this location may be defined relative to the fluid, such that a device operating in a flowing fluid could effectively change its location relative to the fluid by remaining fixed while the fluid flows past it. A third option is for the device to change its orientation 218, which can change the orientation of one or more ports and/or sensors to face towards or away from a particular direction.

Figure 8:
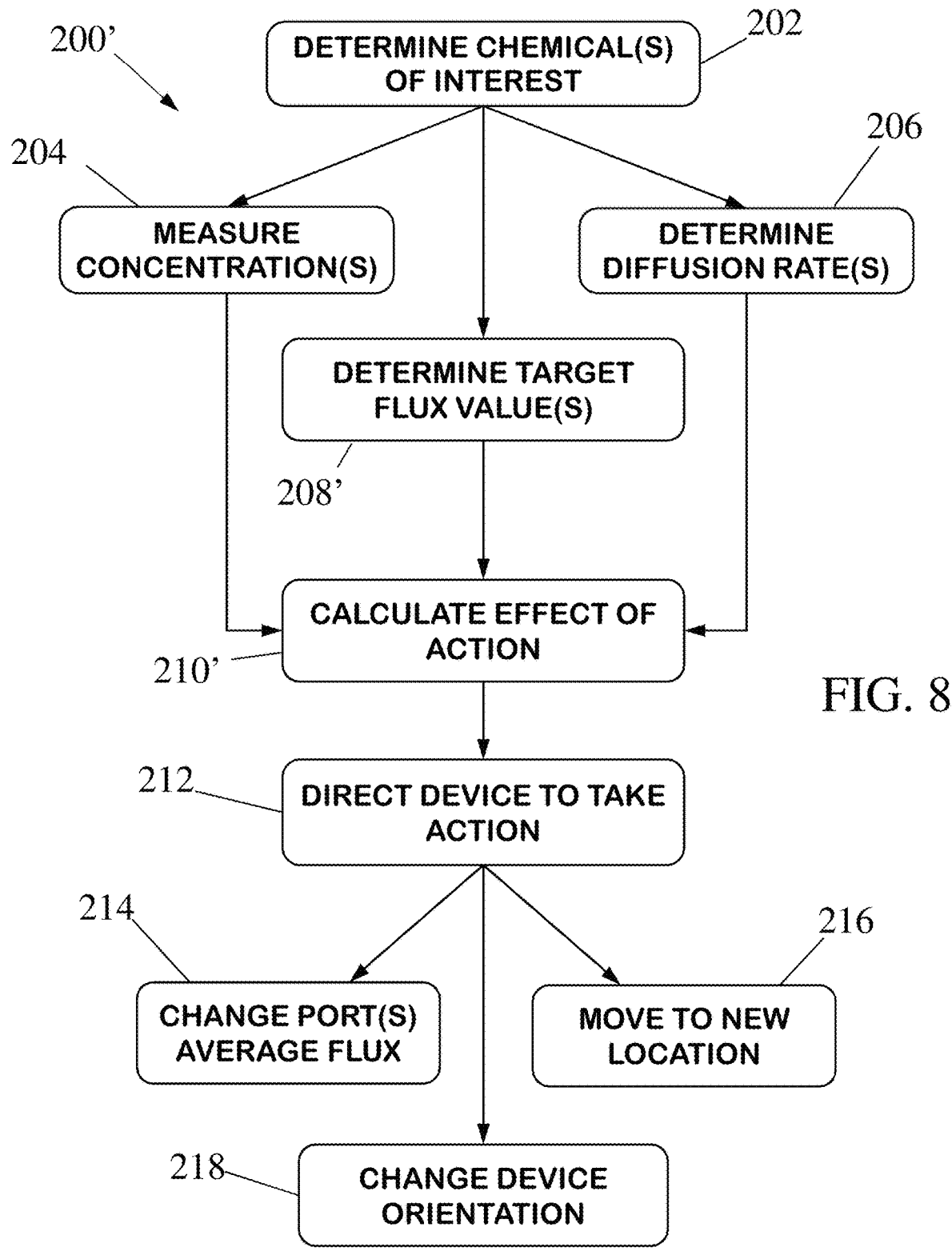
FIG. 8 is a flow chart illustrating a method similar to that of FIG. 6, but where the device is operated to achieve a target flux for the chemical(s) of interest.

FIG. 8 illustrates a method 200' that is similar to the method 200, but where a target flux value for each chemical of interest is determined 208', rather than a target concentration. The calculation 210' determines the effect of one or more possible actions on the flux for each chemical, in order to determine what action is appropriate to achieve the desired flux.

Concentration (as addressed in the method 200) and flux (as addressed in the method 200') are the two most common boundary conditions considered for diffusion applications and simulations. There is a third, generalization that specifies a desired linear combination of concentration and flux (depending on the field, such generalizations may be termed "Robin", "impedance", or "radiation" boundary conditions.) The linear combination can be expressed as: A*concentration+B*flux=desired value, where A and B are constants. When B=0, the value reduces to a specified concentration, when A=0, it reduces to a specified flux. Other generalizations that may be desired in some situations are values for the rate of change of concentration and/or flux over time. Accordingly, it should be appreciated that where the present application refers to desired concentration or desired flux, these terms are intended to include both the value on its own and in combination with the other, and are intended to include both constant values and values for specified rate of change.

Device Design

Figure 9:
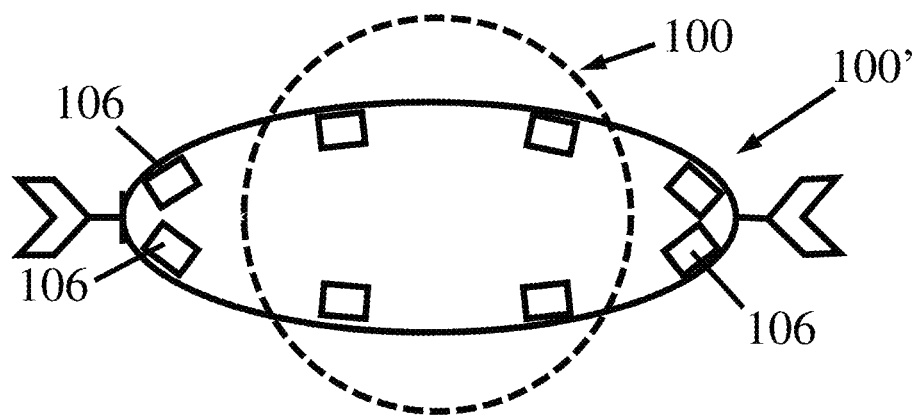
FIG. 9 illustrates one example of a prolate-shaped device which provides a greater separation distance between sensors than is possible with a spherical device of similar volume. Spacing the sensors further can provide greater accuracy when measuring gradients.

Devices can be designed with diffusion in mind, sometimes with huge improvements in performance resulting from optimal designs. Size is obviously important in many scenarios, as larger devices can affect greater areas and have increased flux, as many of the examples herein demonstrate. Feature spacing on a device surface can also be important, and is discussed in more detail herein. Shape can play an important role as well. For example, an optimally-shaped prolate device can detect gradients with greater efficiency compared to an equal volume sphere. FIG. 9 illustrates one example of a device 100' having sensors 106; while having a similar volume to the device 100, the device 100' has an elongated shape, and thus the sensors 106 can be positioned on the device 100' at a greater separation, allowing the device 100' to be positioned in a gradient 190 with sensors 106 positioned at locations where the difference in concentration due to the gradient is greater, providing increased sensitivity.

Additionally, devices could be designed to be reconfigured on-the-fly, such as by using flexible or movable portions of the body, with pistons or other actuators to move such portions to change the configuration for optimal performance under the current situation. For example, the optimal shapes for sensing, influx/efflux, movement, or other activities, may all be different. Although this adds to engineering complexity, there is no reason why a device cannot be designed to adopt different shapes at different times, or to mimic optimal shapes in other ways. For example, sensors could be mounted on the ends of arms (either fixed or extendible/retractable), allowing a spherical device to position sensors as if it were a prolate device.

Also, given the stiffness and versatility of available materials (e.g., silicon, diamond, or carbon nanotubes), device designs need not be limited to shapes similar to those found in nature. For example, much higher aspect ratios could be used, or complex shapes (e.g., toroids or other complex geometrical shapes, including perforate designs) employed which balance diffusion considerations against size limitations, movement issues, the ability to dock with other devices, the ability to couple to various types of waves (e.g., radio or acoustic) for power and communication, and other concerns. For a detailed description of the use of acoustics for power and communication in small-scale devices, see U.S. Pat. Nos. 8,743,659; 8,743,660; 8,755,252; 8,760,972; 8,787,115; 8,837,258; and 10,024,950; all incorporated herein by reference.

The formulas and analyses herein, along with the identification of diffusion-related problems and exemplary solutions, will make apparent many scenarios where particular designs can enhance device performance in the face of diffusion-limited situations.

Movement

Movement relative to salient concentrations is one way to avoid diffusion-limited problems. Whether for measurement purposes, fuel intake, waste product expulsion, or other functions, it may be more efficient to move to an area that has not been as affected by device operation or has an innately different concentration or flux, than to wait for diffusion to restore the necessary concentrations. This will depend on ease and speed of movement, size of device, diffusion coefficients, flux, available power, and other factors, many of which will be unique to a given device or scenario.

Another application of the concept of "moving" to another environment is for the device to remain stationary within a moving environment. For example, if a device were to affix itself to the wall of a vessel containing a fluid flow, the flow could quickly restore local concentrations even in the face of perturbations by the device.

While living organisms are known to affix themselves to substrates, either individually or in groups (e.g., biofilms), due to enhanced logic or information sources, a device could use substantially more sophisticated strategies to determine, for example, when and where to adhere. Some such topics are discussed elsewhere herein, but examples include receiving instructions from other devices or controller devices (e.g., to relay knowledge of local or remote conditions), using internal clocks or maps (e.g., in a medical scenario, a device could use time of day to predict likely blood sugar levels due to meal schedules, which might even vary on weekends or holidays—a level of sophistication no bacteria could hope to achieve), or sensors providing unique data (e.g., sensing unique chemicals or conditions, or sensing standard chemicals or conditions with increased accuracy).

A device may want to avoid a source or sink (which could be environmental, or could be another device) which adversely affects certain concentrations (and, like most of the analyses herein, a similar analysis could be used for the opposite goal or effect; in this case, to seek out a source or sink).

The speeds and distances required to do this can be calculated as follows. In general, in time t, diffusion typically moves a distance of order sqrt(D*t), where D is the diffusion coefficient, while a device moving at speed v goes a distance v t. Thus, outrunning diffusion from a stationary source requires v t>sqrt(D*t), which is equivalent to saying that movement must occur over time t>D/v^2. For example, a device moving 1 mm/s and absorbing oxygen in water (D=2*10^-9 m^2/s) must move for t=2 ms or more.

A device could in theory outrun its own diffusion-based effects. (Dusenbery, "Living at Micro Scale." Harvard University Press, 2011) suggests that, at least with respect to living organisms, this strategy is of little value because most organisms cannot move fast enough to avoid their own effects to a substantial degree, and that organisms under 10 μm receive essentially no benefit from such movement.

Regardless of whether this strategy is useful to micro-organisms, it can be valuable to devices. Devices may have different power levels available, different movement efficiencies, and different goals and priorities than living organisms (e.g., escaping the effects of diffusion may be worth greater energy expenditure). Also note that Brownian motion complicates navigation for micro-organisms. Micro-organisms, even when trying to follow a straight path, may become mis-oriented in a short period of time due to random directional changes caused by Brownian motion. A micro-scale device can overcome this problem in several ways, including orienting itself to an external signal (e.g., a magnetic, or RF, or light field), by using internal gyroscopes, or via communication with other devices which could be used as reference points.

Where a moving device itself is a source or sink and the goal is to mitigate its own effects on either itself or the environment, the analysis is somewhat different than that used for a stationary source or sink. Device size becomes relevant because device size affects the area of concentration change. In the case of a device trying to outrun its own effects, there is no sharp cutoff. Rather, the faster the device moves relative to its size, the less diffusion-limited it becomes. The following equation can be used to approximate the change in flux due to movement:

$$\text{Flux Increase} = \tfrac{1}{2}(1 + (1+2Pe)^{1/3}) \quad \text{(Eq. 4)}$$

Where Pe is the Peclet number expressed as $Pe = L^2 U/D$, to incorporate the relationship of speed to size. L=Length, U=Diameters per second, and D=Diffusion coefficient.

That a device can, at least partially outrun its own effects, suggests that a strategy could be employed where not only could constant movement be used, but also "absorb, move, absorb" cycles can allow greater flux than remaining stationary.

Moving to a More Favorable Environment

Movement to an environment with different characteristics can be a useful strategy. With respect to changing location not to outrun diffusion, but rather to find a generally more favorable environment, a sphere of radius r absorbs chemical (in steady-state) at a rate 4*pi*r*D*C. Moving to a location with higher concentration C is one way to increase absorption (and the same theory applies to efflux, as in all examples herein). For an environment where the diffusion coefficient varies at different locations, another possibility is to move to locations with higher diffusion coefficient. More generally, it may be favorable to move to a location with a larger value of the product D*C, which illustrates the fact that a viable strategy to increase flux can include moving to a location with a lower concentration if that location has an increased diffusion coefficient so that D*C is larger. In other words, flux can be more important than concentration. However, changing flux irrespective of concentration is not always a viable solution because, for example, of situations where concentration must be in a certain range to permit proper device operation.

Living organisms will follow a gradient which leads to a more desired environment in terms of factors such as food, light, or temperature. However, the options for moving to a more favorable environment are more numerous, and the potential behaviors more complex, for a device. There are several reasons for this.

First, devices can be designed to operate in a wider range of environments than living organisms have been observed to tolerate. For example, devices used to clean the insides of industrial pipes could move to areas with temperatures that living organisms could not tolerate. Extremes of cold could be better tolerated as well. And, a device could function in concentrations of various chemicals that would be toxic to a living organism. A device could also seek out environments that are qualitatively quite different (e.g., moving from a liquid to gaseous environment, a more or less viscous environment, or even into vacuum). Another example includes moving into environments that would require high radiation tolerance (including electromagnetic or sub-atomic radiation).

Second, devices may have access to information which living organisms do not, enabling the location of beneficial environments which could not have been found by, e.g., bacteria. For example, a device might store data representing a map of its environment, could possess unique sensors or logic, or could be in contact with other devices or external controllers (e.g., a transceiver connected to a computing means, which may aid in controlling or coordinating one or more devices), any of which could direct it to beneficial environments that living organisms would have no way of locating. This is similar in some cases to the concept of finding a global minimum or maximum rather than getting stuck in a local one, as could happen if navigating solely using gradients.

Adjusting Device Spacing

In the case of multiple devices, optimal inter-device distance may minimize diffusion-related problems. For example, if the devices are far enough apart, it may be the case that a single device would have no need to change location as the concentrations available locally, even after prolonged operation, are sufficient.

Devices will not always be able to minimize their effect on chemical concentrations so as not to adversely affect their neighbors or the environment. For example, if multiple devices which are interacting with each other are competing for chemical power, there is a trade-off between being far enough apart to get sufficient fuel versus being close enough together to perform a designated task. Another aspect of multiple device coordination is communication. When devices are farther apart, they will need more power for communication, or if using the same power, will reach fewer neighbors or transmit less information, yet if they get closer to facilitate communication, they may use up available fuel, increase local waste, raise local temperatures, or have other effects which cannot be completely compensated for by diffusion. Similar concerns apply to not just inter-device communication, but communication with, or receiving power from, an outside transceiver, which may impose distance limitations. In such cases, compromises will have to be made between spacing, operating envelopes, and operational goals, and the optimal device behavior will be application-dependent.

While application-dependent, the basis for such decisions starts with understanding the impact multiple devices have on each other and the environment, in a given configuration. Consider, as an example, a spherical area containing many devices. A group of devices occupying radius R can absorb at most 4Pi*R*D*C, compared to maximum 4Pi*a*D*C for a single, isolated device. Thus, the maximum group absorption relative to that of a single isolated device is R/a. Due to the fact that devices reduce concentration appreciably out to several diameters, the total volume of devices within the sphere can be quite small relative to the overall group volume, yet still cause large concentration decreases towards the sphere's center.

For example, if R/a=100 (meaning, the group spans a volume whose radius is 100 times that of single device), there are 10,000 devices, and the total device volume is 1% of the group volume, given a uniform distribution of flux-limited devices, the concentration inside the group is close to 0 for distances of less than 80 times the individual device radius from the center of the group. In other words, most of the devices are completely starved in such a configuration. Obviously, this would be a problem if all devices need to absorb some amount of the relevant chemical. Such situations can be remedied by varying various parameters. The devices can be spaced farther apart (either by reducing their number, or increasing the overall group volume), their flux can be reduced (including via changes in duty cycle), or their spacing can be adjusted.

Figure 10:
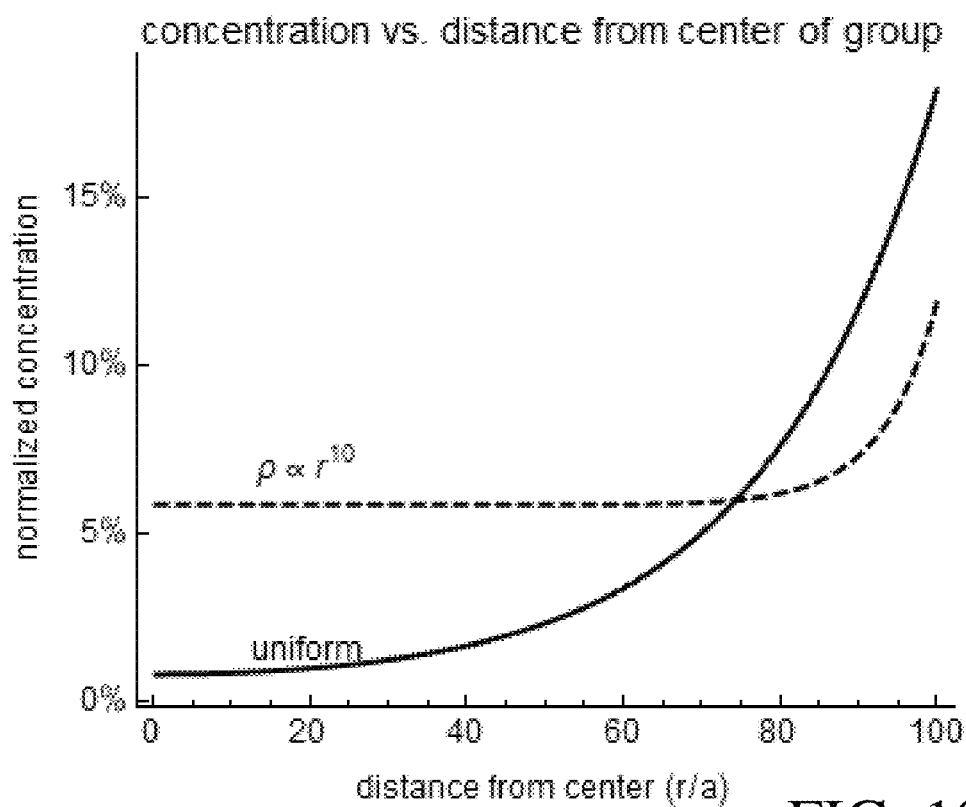
FIG. 10 is a graph showing concentration as a function of distance from the center of a group of devices, comparing an example where the devices are evenly distributed and an example where the devices are preferentially located towards the perimeter of the group to provide a more even concentration throughout the volume occupied by the group.

Uniform spacing, assuming flux-limited devices, will create lower concentration and thus lower flux, towards the center of the group. If similar concentrations are desired for all devices within the group, the distribution of devices must be skewed towards the surface of the group volume, with relatively few devices towards the group center. FIG. 10 compares examples of the concentration as a function of distance from the center of a group or swarm of devices, showing the case where the devices in the group are uniformly distributed (solid line) and the case where the device placement is skewed toward the outside of the group volume (dashed line). FIGS. 11A-D illustrate a plot of a uniform distribution (shown in FIGS. 11A & 11C) compared to a non-uniform distribution (shown in FIGS. 11B & 11D). The exact distribution which provides for similar concentrations throughout the group volume will vary with group size, device number, and device size, but can be solved for numerically. For example, to generate the graph shown in FIG. 10 and the plots shown in FIGS. 11A-D, concentrations were calculated for a group volume that has a radius 100 times that of the individual devices, with the total volume of the individual devices occupying 1/1000 of the total group volume. The graph shows concentrations for a uniform density and for the case where the density varies approximately as $r^{10}$, where r is the distance from the center of the group. Using that distribution, most of the group volume's interior has approximately the same concentration (as indicated by the dashed line in FIG. 10), although the outermost region is still higher than the center. Obviously, scaling device distribution as $r^{10}$ is severely non-uniform. Rather, it forms a shell of devices towards the periphery with virtually no devices in the center, as shown in FIGS. 11B & 11D. If the devices are not flux-limited (or any of the other parameters vary), the distribution can be significantly different.

Adjusting Flux

Rather than adjusting spacing to permit all devices in a cluster access to similar concentrations, flux can be adjusted. In a group of devices distributed evenly in a spherical region, if similar flux through each device is desired, each device can only be permitted to absorb a fraction of what it would if it were diffusion-limited. Specifically:

$$\text{Individual Device Absorption} \leq 2/(2+3(R/a)^2 fv) \quad \text{(Eq. 5)}$$

where fv is the fraction of group volume occupied by devices.

Figure 12:
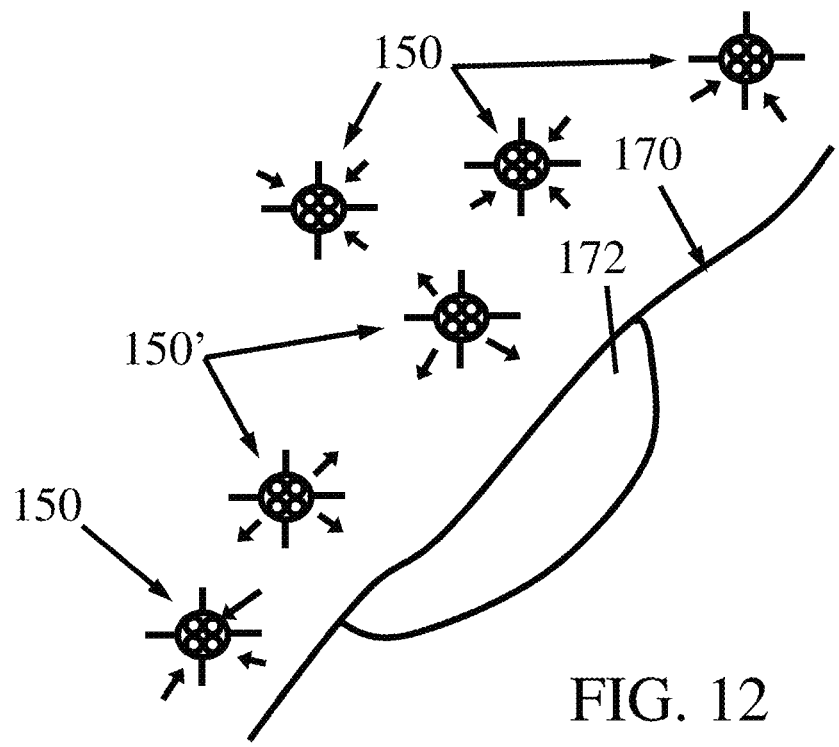
FIG. 12 illustrates another example of "swarm" behavior, in this case a situation where a number of devices operate in coordination, to change chemical concentrations at a site of interest. Two devices operate to increase concentrations, while the surrounding devices operate to reduce concentrations.
Figure 13:
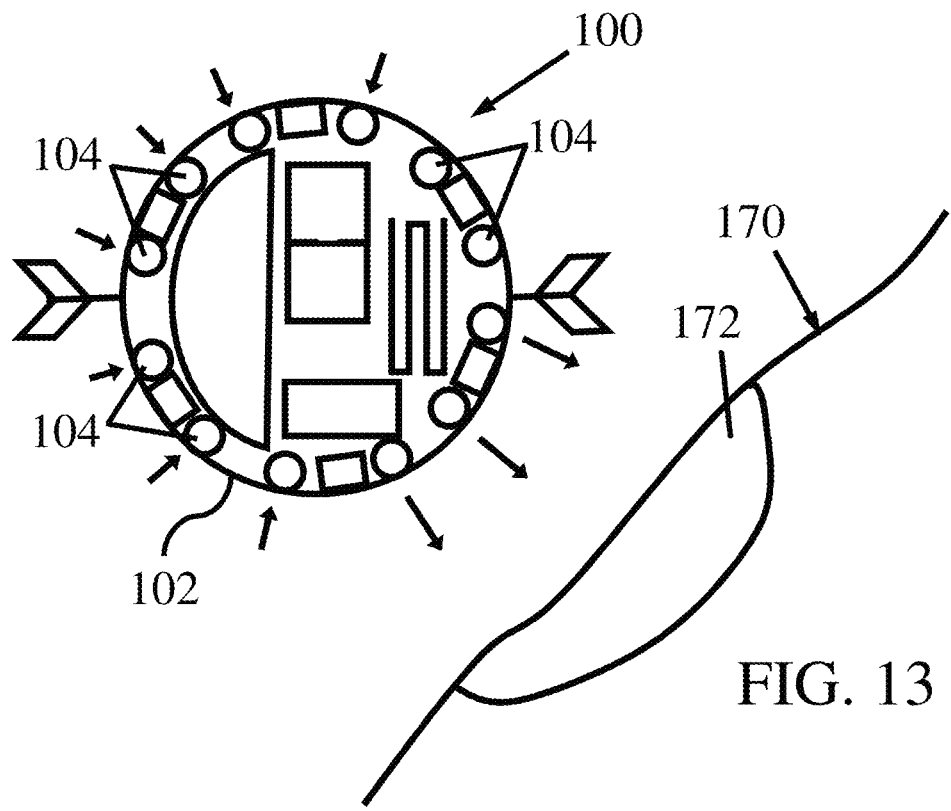
FIG. 13 illustrates a situation similar to that shown in FIG. 12, but where a single, larger device is employed rather than a number of smaller devices. In this case, selected ports facing the site operate to increase concentration, while other ports on the device operate to reduce concentration.

Note that when dealing with multiple devices, or multiple ports on the same device, flux could also be in different directions in different devices. For example, consider a scenario such as shown in FIG. 12 where multiple devices 150 operate to deliver a chemotherapeutic agent to a region of tissue 170 where a cancer cell 172 has been detected; in this case, treatment requires some minimal concentration at a particular location of the cancer cell 172. However, due to the toxicity to neighboring cells of the tissue 170, it is also desired to keep concentrations to a minimum in other locations. The group of emitting devices 150' can be surrounded by a group of absorbing devices 150, so that any of the chemical not taken up by the cancer cell 172 is captured by the outer group of devices 150 rather than diffusing into other cells. In an alternative scheme, shown in FIG. 13, a device 100 operates its ports 104 differently on different sides of its body 102, such that ports 104 operate to emit a chemical on one side facing the cancer cell 172, and operate to absorb the chemical on the other side, thereby reducing the exposure of chemical to the surrounding tissue 170. An alternative scheme for changing concentrations from one side of a device to another (particularly when the device itself is not releasing the chemical) would be for the device to employ internal pumps and conduits that serve to actively transport an absorbed chemical from the absorbing surface to the emitting surface, thereby increasing concentration near the emitting surface more than can be provided for by diffusion. In such case, if the concentration at the absorbing surface happens to be lower than at the emitting surface, diffusion tends to move the chemical away from the region outside the emitting surface. Transport of the chemical could also be enhanced if the interior of the device has a larger diffusion coefficient than the fluid around it, so that the chemical can diffuse faster through the device than through the surrounding fluid.

Adjusting Duty Cycle

Duty cycle can also be adjusted, by itself, or in conjunction with flux. Perhaps against intuition, a device running continuously (meaning, a 100% duty cycle) at flux X will affect nearby concentrations more than a device running at a 50% duty cycle with flux 2×. Although both scenarios produce the same average flux, higher flux for shorter time periods creates a steeper depletion gradient near the device. This steeper gradient is restored faster by diffusion (although over time, repeated high flux, or "burst" cycles actually permit less flux than a 100% duty cycle). The relationship between flux and concentration gradient magnitude can be represented by the equation:

$$J = -D \nabla C \quad \text{(Eq.6)}$$

Where J is flux, D is the diffusion coefficient, ∇ is the gradient operator, and C is density (which may represent different quantities in different situations, for example, chemical concentration, number of particles, energy, charge, etc.).

Since maximum flux at a device's surface will still be diffusion limited, this strategy cannot be used to reduce concentration changes an arbitrary amount, but to the extent that device operation would typically not be flux-limited, reduce duty cycle and increasing flux can be a valuable strategy.

This strategy not only allows, at least for some time, a reduction in the local concentration changes caused by a device, and operating in high-flux burst cycles can, for example, allow powering of transient functions with high power requirements, without having to store power. For example, a device may need to communicate with other devices only periodically, and could use more power, thus increasing transmission capabilities, while operating in burst mode, without resorting to stored power.

Figure 14:
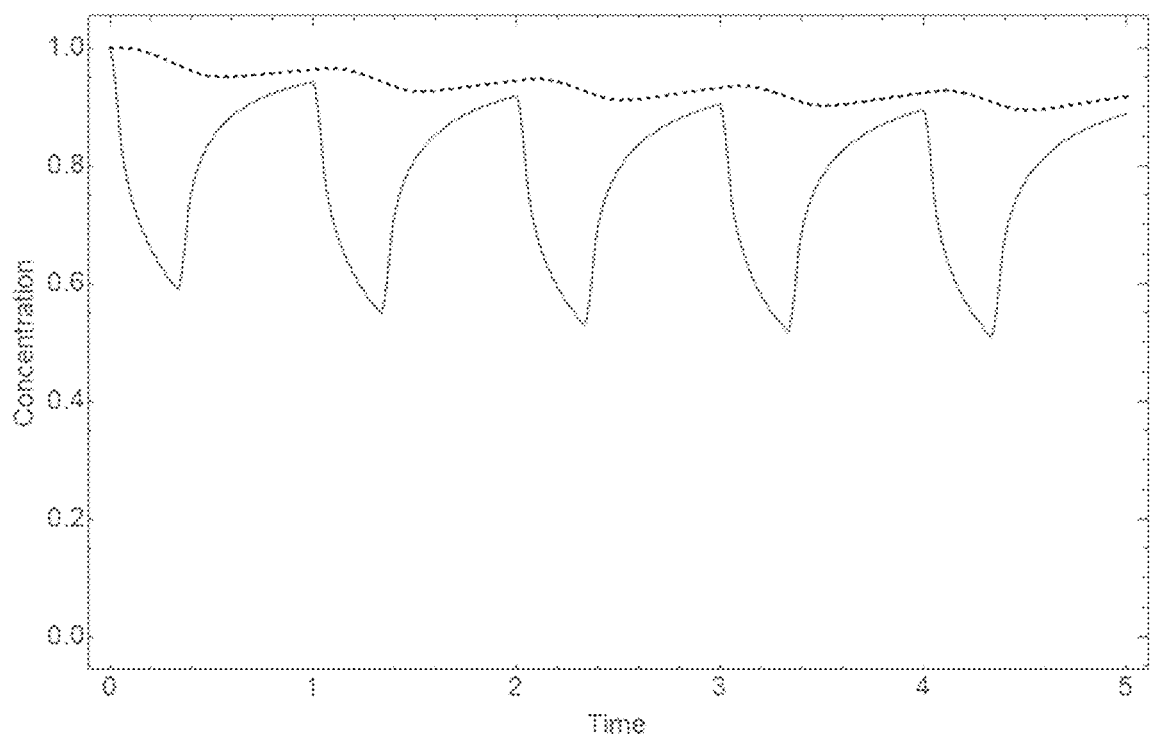
FIG. 14 is a graph illustrating the effect of periodic operation of one or more ports on concentration at the surface of a device and at a distance of one radius.

FIG. 14 illustrates the effect of an absorbing sphere on concentration 1 radius away, when operated in a periodic burst mode. Concentration is relative to environmental concentration an infinite distance from the device. The solid line indicates concentration at the sphere surface, while the dashed line indicates concentration at a distance one radius away. While a steady state would eventually be reached, there can be substantial benefits in reduced perturbation of the surrounding environment by using some form of duty cycle. To investigate other parameters, the following Mathematica 9 code may be used:

```
(* Start Code *)
With[{
T=1, (* duty cycle time *)
f=⅓,(* fraction of duty cycle sphere is absorbing *)
\[Delta]s=.05, (* on/off switching time,
which must be less than Min[f,1−f]T *)
R=1, (* absorption rate *)
numPeriods=5},(* number of duty cycles to compute *)
Module[{absorption, concentration},
(* fraction of maximum absorption during duty cycle *)
absorption[t_?NumberQ] :=
   Module[{\[Tau]=Mod[t, T]},
   \[Piecewise]{
      {Min[1, \[Tau]/\[Delta]s], 0<=\[Tau]<=f T},
      {Max[0, 1 −(\[Tau]−f T)/\[Delta]s], f T<\[Tau]}
   }
];
(* solve diffusion equation *)
concentration=NDSolveValue[{
\!\(
\*SubscriptBox[\(\[PartialD]\), \(t\)]\(c[x, t]\)\)==(−1+x)
^4 \!\(
\*SubscriptBox[\(\[PartialD]\), \(x, x\)]\(c[x, t]\)\),
(*
scaled diffusion equation *)
c[x, 0]==1,(* initial uniform concentration *)
Derivative[1, 0][c][0, t]==R absorption[t], (* switch on/off *)
c[1, t]==1 (* concentration far from sphere *)
},
c, {x, 0, 1}, {t, 0, numPeriods T},
Method −>{"MethodOfLines",
   "DifferentiateBoundaryConditions"−>False} ];
(* plot concentration vs. time for several duty cycles *)
Plot[
Evaluate[Table[concentration[1−1/r, t], {r, {1, 2} }]],
{t, 0, numPeriods T},
AxesOrigin −>{0, 0},
BaseStyle −>24,
Frame −>True,
FrameLabel −>{"Time", "Concentration "},
ImageSize −>800,
PlotStyle −>{Thick, Dashed},
PlotLegends −>
Placed[LineLegend[{"Absorbing Sphere Surface",
   "One Radius Away" }, LabelStyle −>24], {0.5, 0.3}]
]
]]
(* End Code *)
```

Anticipatory Behavior

In many cases, devices are designed to have some ability to store power, waste, payloads, or other factors. When available, such storage capacity leads to the ability to anticipate diffusion-limited problems and at least partially compensate.

For example, based upon timing, communication from outside devices, positional data, trends in concentrations, or other information, a device may know that a period of low fuel availability is approaching. This can trigger behavior to store as much fuel as possible, which could mean, for example, absorbing fuel faster, or reducing current power usage.

Fuel is simply one example, and the ability of devices to store chemicals, communicate, store data, or employ complex logic also allows many other anticipatory behaviors. Other examples of similar strategies to pre-emptively compensate for diffusion-limited scenarios include charging batteries, offloading data which will require communication power, emptying waste storage, adjusting flux or duty cycle, moving (or affixing so as to not move), adjusting inter-device spacing in a group, changing behaviors between catching and releasing a particular chemical, catching and destroying the chemical, and catching and holding the chemical, or any of the other strategies discussed herein.

Correcting Sensor Data

Figure 15:
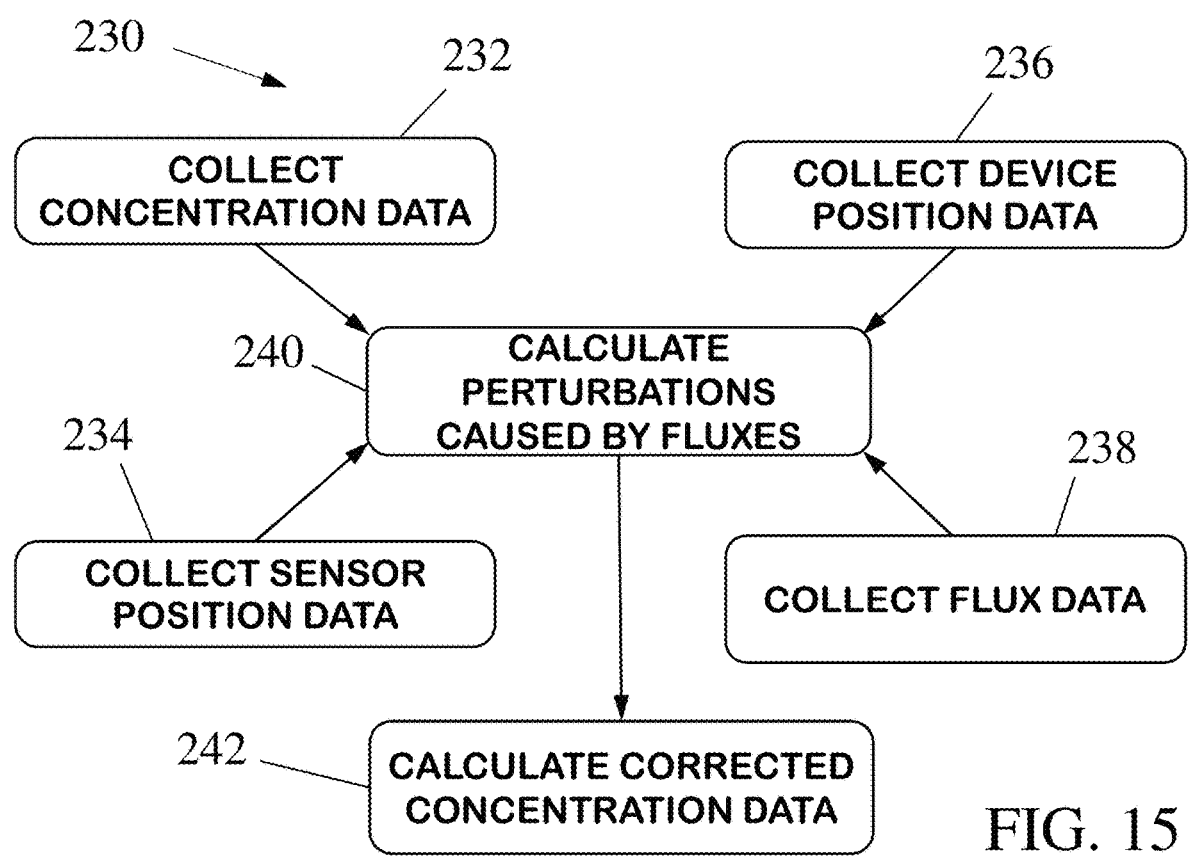
FIG. 15 is a flow chart illustrating a method for correcting sensor measurements taken by a device.

In some cases, the action of one or more devices acts to perturb measurements of one or more chemicals of interest. FIG. 15 illustrates one example of a general method 230 for correcting sensor data. The method 230 illustrated makes use of a range of data, and includes collecting data on the current concentration 232, data on the position of one or more sensors 234, data on the position of one or more devices 236, and data on the flux 238 of the device(s). Depending on the particular situation, not all of these data may be needed to obtain corrected sensor data. Based on the collected data, the perturbations in concentration (as measured by the sensors) caused by fluxes is calculated 240, and these calculated perturbations can then be used to correct the sensor data 242 to compensate for such fluxes. Some examples of perturbation effects are discussed below.

Proxy or Alternate Measurements

Proxy or alternate measurements may have use in mitigating diffusion-induced error. For example, assume a device is measuring the concentration of a chemical of interest which is being perturbed by its own actions, and/or by the action of other devices. The problem will be more severe where device flux is high compared to concentration, meaning, all other things being equal, low concentrations will be proportionately more perturbed.

To avoid this problem, one strategy would be to use a higher-concentration chemical as a proxy (assuming the two concentrations are correlated with the desired data). This would allow more accurate measurement of concentrations and gradients.

The idea of proxy measurements does not apply only to chemicals where one has a high concentration and the other a low concentration. For example, measurements could be made of alternate chemicals which are chosen not because of their concentration, but because they are simply less perturbed. For example, assume that both O2 and glucose concentrations are equally correlated with some information being gathered by a device. Assuming that there are devices in the area which may be perturbing the concentration of glucose, but not O2, one could measure O2 concentrations to avoid diffusion-related perturbation errors altogether.

Figure 16:
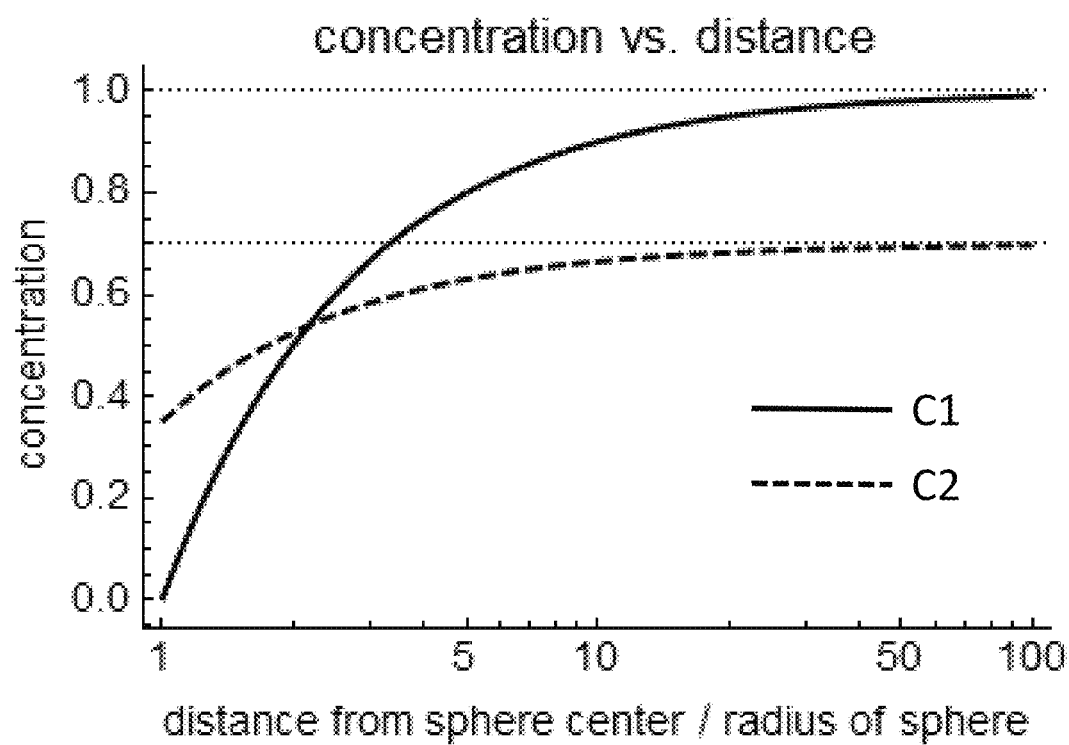
FIG. 16 is a graph illustrating concentrations of two different chemicals at various distances from a device when present in the environment at different concentrations, and being absorbed at different rates.

There is also the situation to consider where the flux for one chemical is higher, but its concentration is also higher, leading to a distance-dependent relationship in terms of which chemical is more perturbed. For example, FIG. 16 demonstrates the concentration versus distance relationships for two chemicals, C1 and C2, which are being absorbed at the surface of a device. Concentration is relative to environmental concentration an infinite distance from the device (a logarithmic scale for distance is employed in FIG. 16), where the relative concentrations of C1 and C2 are 1.0 and 0.7, respectively (arbitrary concentration units). The assumptions are that, due to differing absorption rates, the concentration of C1 at the device surface is 0, while the concentration of C2 at the device is 0.5 (relative to the concentration of C2 at infinite distance, which is 0.7*C1, so the concentration of C2 at the device is 0.35*C1 at an infinite distance). In this scenario, if one wanted to determine which concentration was more perturbed, and by how much, the answer would depend on the distance from the device. Under about 2.2 radii, C2 is present at a higher concentration, even though in the general environment its concentration is lower. This is due to the lesser absorption of C2 by the device. Over about 2.2 radii, the concentration of C1 is higher.

However, one has to know that perturbations will exist in the first place to know how to design devices, what concentrations may be preferable to measure, how to reverse-engineer the actual environmental concentrations where that is the goal, and what actions might be taken to allow more accurate sensing or more efficient functioning (e.g., moving away from devices that are confounding measurements, depleting fuel, or producing excess waste). Note that while the examples herein generally discuss the measurement of one or two concentrations, any number of concentrations may be measured, and of course, are not limited to chemical concentrations but could also include heat, charge, etc., as could any of the examples discussed.

Proximity of Devices of Varying Size

As previously discussed (see FIG. 6) one problematic case where diffusion could hamper device operation involves a smaller device approaching a larger one (or an aggregate of smaller devices). A device materially affects concentrations out to several times its diameter. So, if a larger device is causing problematic concentration changes out to several radii, a smaller device approaching the larger device will move through an affected region which is large compared to the smaller device size. For example, the smaller device could be completely inside a region with insufficient fuel, high waste concentrations, high temperatures, or skewed analyte concentrations. On the other hand, the smaller device will tend to have less effect on the larger device (although multiple smaller devices could more adversely impact a larger device).

One way to address these issues is for the larger device to temporarily reduce (or cease) its activity, either uniformly, or if practical, most importantly on the side facing the small device. A reduction in global or local activity would allow diffusion to at least partially restore the normal environment.

Alternatively, the larger device could compensate for its own activities, or even go beyond that, in creating a more favorable environment for the smaller device. For example, if the larger device had depleted the local area of fuel, but has onboard reserves, those could be released for use for the smaller device. Similarly, waste could be stored instead of released, and "catch and release" (rather than, for example, catch and store, or catch and destroy) methods could be used to allow the larger device to say, measure analytes, without markedly perturbing their concentration.

Again, the solutions to such problems require first an accurate understanding of exactly when such issues even exist, quantitative assessment of the problem, and then strategies to deal with the problem, whether that be avoidance (e.g., keep the devices far apart), algorithmic solutions to optimize distance and behavior, optimized design of the devices themselves, adjusting raw sensor data based on calculated and/or observed perturbations, or any combination thereof.

Feature Spacing and Rotation

The location of features on a device is analogous to inter-device spacing problems. The scale may be different (e.g., features on a single device might be nanometers apart instead of microns), and the exact solution to the diffusion problem may be somewhat more complex due to the effect of the device itself, which impedes diffusion in some directions in a manner similar to the example of a small device approaching a larger device. However, the solutions to such problems will be apparent given the teachings herein.

For example, influx/efflux ports for the same chemical should not be clustered together, but rather spaced out over the surface of the device if achieving the greatest flux is a goal. Also, having multiple influx or efflux points which are selectable would allow a device to take advantage of concentrations which differ from one side of the device to the other, or to preferentially reduce or remediate its own effects on the environment (as when a device needs to create a favorable environment for another nearby device).

This discussion also suggests the strategy of a device rotating to take advantage of certain effects or conditions. For example, even with only one influx/efflux port, or several ports that cannot be individually controlled, spaced far enough apart that concentrations around the device are non-uniform, a device could change its orientation to increase its own flux, or to minimize or maximize its effect on the local environment (e.g., pointing ports away from another proximate device or other feature of the environment so as not to adversely affect it, or pointing ports toward a payload recipient). Note that in the case of multiple ports with the ability to change the flux or duty cycles of some ports and not others, such changes amount to movement of the ports or rotation of the device, and will be considered part of device positioning.

Accounting for Directionality

The effects of changes in diffusion-related phenomena can be directional. For example, in moving fluids where upstream devices are consuming a chemical which affects the concentration available for downstream devices, more than vice versa. Or, the environment may be inherently anisotropic.

Counter-intuitive effects may be present in such scenarios. For example, for elongated devices extending along the direction of the flow, parts at the downstream end may have somewhat more available chemical than those in the middle (see FIG. 4 of (Hogg and Freitas, "Chemical Power for microscopic robots in capillaries," Nanomedicine: Nanotechnology, Biology and Medicine, 2, 2010)), because even though more upstream absorption is occurring, diffusion brings chemicals back to the downstream end of the device more effectively than to areas in the middle of the device. The magnitude of the effect depends on the ratio of flow speed to the diffusion coefficient. This ratio is referred to as the Peclet number. Note that different phenomena (e.g., mass transport of different chemicals, or mass transport compared to, e.g., heat transport) may have different Peclet numbers, leading to double diffusive convection. Other effects may also need to be considered, such as Taylor Dispersion. (Wunderlich, Nettels et al., "Taylor dispersion and the position-to-time conversion in microfluidic mixing devices," Lab on a Chip, 1, 2014)

Generalization of Scenarios

Figure 17:
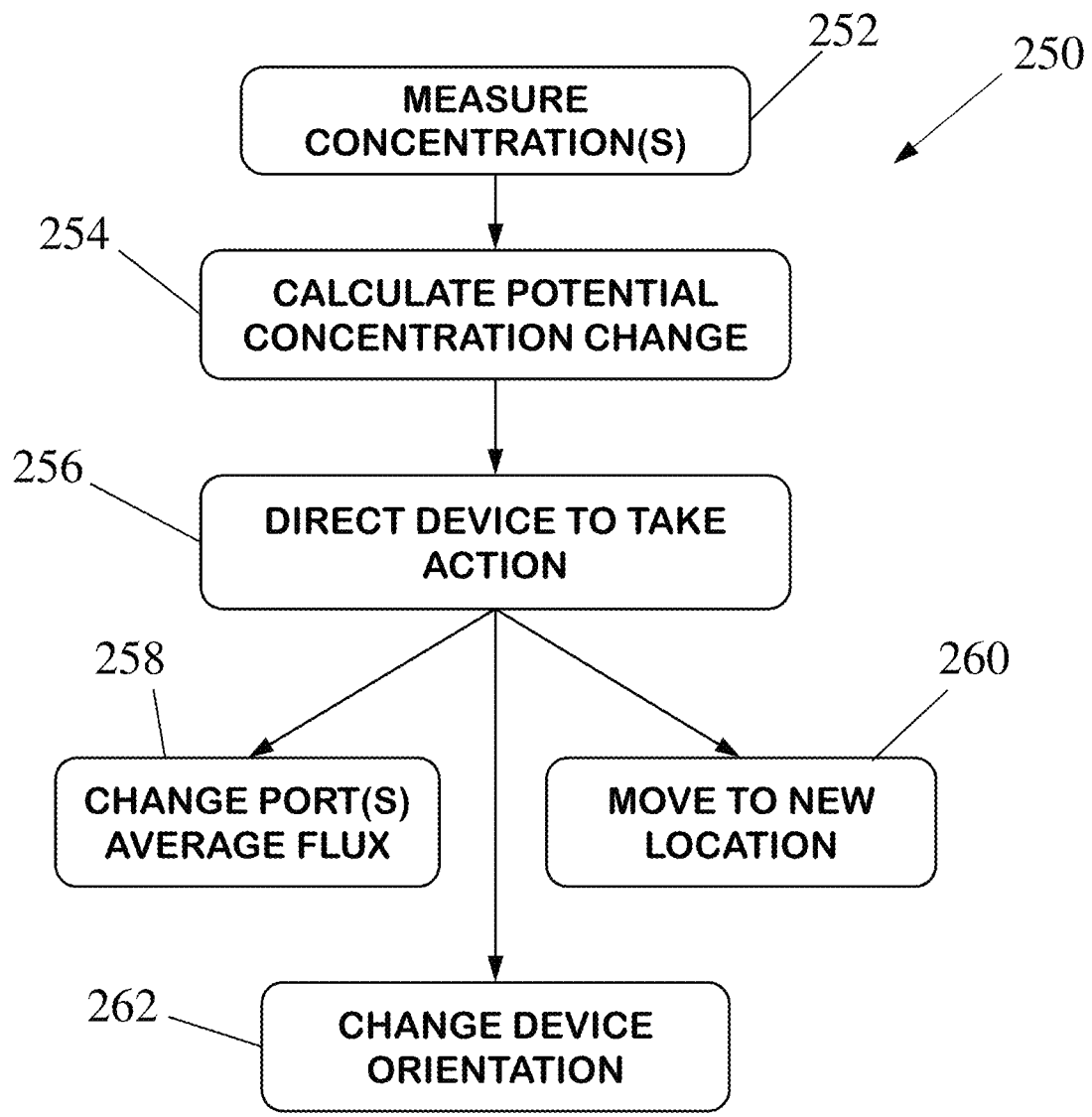
FIG. 17 is a flow chart showing a general method of operating a device in a diffusion-limited condition.

FIG. 17 illustrates a general method 250 for operating a device with consideration to the various diffusion-related factors discussed above. First, measurements are taken 252 of one or more chemicals of interest to the particular intended mission of the device. Taking into account the diffusion rate of at least one of such chemicals and responsive to the measured concentration(s) 252, calculations are made 254 to determine the potential concentration change that can be achieved for the device. Based on the calculation 254, the device is directed 256 to take an appropriate action to change the flux of at least one port. As with the methods (200, 200') discussed above, possible actions include changing operational parameters (flux, duty cycle) to directly change the average flux 258 of one or more port(s), moving to a new location 260 (where a difference in concentration and/or diffusion rate has the effect of changing the flux of the port(s), even if operating parameters remain constant), and/or changing the device orientation 262 (where such change exposes the port(s) to a region in the fluid with a different concentration and/or diffusion rate, which again has the effect of changing the flux of the port(s) under the same operating parameters).

Most of the examples provided herein discuss a single device and its interaction with concentrations in the environment, two devices and their effects on each other, or multiple devices of the same size in a group bounded by a regular shape (e.g., a sphere). And, while discussed, complicating factors such as convection (including double diffusive convection), fluid flow, and viscosity, temperature or other changes that affect diffusion coefficients, are not explicitly included in the mathematical examples presented. These are merely simplifications for clarity, and given the teachings herein, can routinely be accounted for using the appropriate modeling tools. Each device need not be of the same size, nor cause the same flux, or even operate on the exact same set of concentrations. Group volumes can be of any shape. And, the environment need not be the same with respect to location or time.

Carrying Out Calculations and Communication

Many of the exemplary scenarios described herein require computations to model concentrations in light of diffusion and related phenomena such as fluid flow or convection. There are several options for carrying out these calculations and allowing a device to then take advantage of the results. In some cases, pre-computing may be possible, such as when concentrations, diffusion coefficients and other variables are known ahead of time, and are unlikely to change substantially. Or, simple rules may suffice, not requiring complex modeling. In such cases, the data may be stored in the device, or communicated to the device at the appropriate time. In other cases, due to a changing environment, changes in device position, number, flux, evolving operational goals, or other factors, real-time calculations may be desired.

In some cases calculations may be carried out internally by the device, alone or in concert with other devices. In other cases, computations may be carried out externally. Such computations may be carried out via any appropriate means. For example, a personal computer, a server or cluster of servers, specialized hardware including ASICs, GPUs, quantum computers, or mechanical logic (e.g., rod logic, mechanical link, flex, or cable logic such as taught in US 2017/0192748, incorporated herein by reference), coupled with appropriate memory means, such as SRAM, DRAM, mechanical memory (such as taught in US 2017/0192748) or any of many others types of computing and memory known to the art or which may be developed in the future may all be used. The necessary data or control signals may also be communicated to or from the device in any of various ways, including electromagnetic, acoustic, or magnetic signals, or other communication paradigms known to the art or which may be developed in the future. And of course, combinations of pre-computation and real-time computation may be used, as may be combinations of where and how computations take place, and how data is communicated to or from a device. Minimizing computing requirements of the device itself can allow for reduction in size, energy consumption, waste heat, etc.

Although the present invention has been described in considerable detail with reference to certain preferred embodiments thereof, other embodiments are possible. Therefore, the spirit and scope of the appended claims should not be limited to the description of the preferred embodiments contained herein.

BIBLIOGRAPHY

Amirouche, F., Zhou, Y., et al. (2009), "Current micropump technologies and their biomedical applications", Microsystem Technologies.

Behkam, B. and Sitti, M. (2007), "Bacterial Flagella-Based Propulsion and On/Off Motion Control of Microscale Objects", Applied Physics Letters.

Choudhary, V. and Iniewski, K., (2013), "MEMS: Fundamental Technology and Applications," CRC Press.

Dusenbery, D. B., (2009), "Living at Micro Scale: The Unexpected Physics of Being Small,"

Cambridge, Mass., Harvard University Press.

Freitas, R., (1999), "Nanomedicine, Volume I: Basic Capabilities," Landes Bioscience.

Ghodssi, R. and Lin, P., (2011), "MEMS Materials and Processes Handbook," Springer.

Hogg, T. (2007), "Coordinating microscopic robots in viscous fluids", Autonomous Agents and Multi-Agent Systems.

Hogg, T. and Freitas, R. (2010), "Chemical Power for microscopic robots in capillaries", Nanomedicine: Nanotechnology, Biology and Medicine.

Jones, C. W., Tsuji, K., et al. (1998), "Organic-functionalized molecular sieves as shape-selective catalysts", Nature.

Lindroos, V., Franssila, S., et al., (2010), "Handbook of Silicon Based MEMS Materials and Technologies," William Andrew.

Martel, S., Mathieu, J.-B., et al. (2007), "Automatic navigation of an untethered device in the artery of a living animal using a conventional clinical magnetic resonance imaging system", Applied Physics Letters.

Martinez, C. and Corma, A. (2011), "Inorganic molecular sieves: Preparation, modification and industrial application in catalytic processes", Coordination Chemistry Reviews.

Medvedev, E. S. and Stuchebrukhov, A. A. (2006), "Kinetics of proton diffusion in the regimes of fast and slow exchange between the membrane surface and the bulk solution", J Math Biol.

Morris, J. and Iniewski, K., (2013), "Nanoelectronic Device Applications Handbook," CRC Press.

Nguyen, N.-T., Huang, X., et al. (2002), "MEMS-Micropumps: A Review", Journal of Fluids Engineering.

Paprotny, I. and Bergbreiter, S., (2013), "Small-Scale Robotics From Nano-to-Millimeter-Sized Robotic Systems and Applications," Karlsruhe, Germany, Springer.

Prince, J., (2011), "Fast Diffusion in Porous Media," University of Reading, School of Mathematical and Physical Sciences.

Sakar, M., (2010), "MicroBioRobots for Single Cell Manipulation," University of Pennsylvania.

Schulz, M., Shanov, V., et al., (2013), "Nanotube Superfiber Materials: Changing Engineering Design," William Andrew.

Sharapov, V., Sotula, Z., et al., (2013), "Piezo-Electric Electro-Acoustic Transducers," Springer.

Strijkers, G. and Nicolay, K., (2010), "Handbook of Nanophysics: Nanomedicine and Nanorobotics," CRC Press.

Wunderlich, B., Nettels, D., et al. (2014), "Taylor dispersion and the position-to-time conversion in microfluidic mixing devices", Lab on a Chip.

Zhang, C., Xing, D., et al. (2007), "Micropumps, microvalves, and micromixers within PCR microfluidic chips: Advances and trends", Biotechnol Adv.

The invention claimed is:

1. A method for operating a plurality of devices in a fluid environment where a chemical of interest has a rate of diffusion that is sufficiently low, with respect to chemical influx attainable by absorption action of a selected device in the plurality having at least one port, that such absorption can materially affect concentrations of the chemical of interest in the fluid environment within one radius of the selected device, the method comprising the steps of:

sensing a value for a selected parameter related to concentration of the chemical of interest in the fluid environment at the location of the selected device, the sensed parameter being selected from the group of: concentration, flux, and a parameter that combines concentration and flux; and responsive to the sensed value of the selected parameter, directing the selected device to take at least one action to change the rate of absorption of the chemical of interest by at least one port of the selected device, said at least one action including an action selected from the group of:

moving relative to the fluid environment to a previously presented location having a different concentration of the chemical of interest, thereby causing a different rate of absorption, moving to a previously presented location relative to another device in the plurality that is actively absorbing the chemical of interest;

changing orientation relative to the fluid environment to expose a selected port that is absorbing the chemical of interest to fluid having a different concentration of the chemical of interest, thereby causing a different rate of absorption for the selected port;

changing orientation relative to another device in the plurality that is actively absorbing the chemical of interest; and changing the influx rate of one or more influx ports of the selected device.

2. The method of claim 1 wherein said at least one action includes changing the influx rate of at least one port of the selected device.

3. The method of claim 1 wherein said at least one action includes changing the duty cycle of at least one port of the selected device.

4. The method of claim 1 wherein said at least one action includes activating a positioning means to rotate the selected device, thereby changing the orientation of at least one port of the selected device with respect to the fluid environment.

5. The method of claim 1 wherein said at least one action includes activating a positioning means to change the location of the selected device with respect to the fluid environment.

6. The method of claim 1 wherein said step of sensing is performed using at least one sensor located on the selected device.

7. The method of claim 1 wherein said step of directing directs the selected device to increase levels of chemicals stored within the selected device.

8. The method of claim 1 wherein said step of directing directs the selected device to operate with different absorption rates of the chemical of interest at different locations on the selected device's surface.

9. The method of claim 1 wherein said step of sensing is performed using a plurality of spatially-distributed sensors located on the selected device, where the sensors are responsive to a common parameter.

10. The method of claim 9 wherein the plurality of spatially-distributed sensors used to perform said step of sensing is distributed in an elongated shape suitable for gradient detection.

11. The method of claim 1 wherein said step of directing directs the selected device to operate to provide influx of the chemical of interest at one location on the selected device and efflux of the chemical of interest at another location on the selected device.

12. A method of operating a device in a fluid environment where a chemical of interest has rate of diffusion that is sufficiently low, with respect to chemical influx attainable by operating the device, that operation of the device can materially affect concentrations of the chemical of interest in the fluid environment within one radius of the device, the method comprising the steps of:

determining an initial value of a selected parameter related to concentration of the chemical of interest, such parameter being selected from the group of concentration, flux, and a parameter that combines concentration and flux;

determining a diffusion coefficient of the chemical of interest in the fluid environment at the location of the device;

determining a target value for the selected parameter in the fluid environment at the location of the device; and directing the device to take at least one action to bring the value of said selected parameter closer to the determined target value in the fluid environment at the location of a selected port on the device, such at least one action being selected from the group of:

changing the rate of influx of selected port to change the concentration of the chemical of interest in the fluid environment at the location of the selected port;

moving to a location having a different concentration of the chemical of interest, thereby allowing a different rate of absorption; and changing the orientation of the device to change the position of the selected port with respect to the fluid environment to expose the selected port to fluid having a different concentration of the chemical of interest, thereby allowing a different rate of absorption.

13. The method of claim 12 wherein said at least one action includes changing the orientation of the selected device to change the position of the selected port with respect to the fluid environment.

14. The method of claim 12 wherein said at least one action includes moving the selected device to a location having a different concentration of the chemical of interest.

15. The method of claim 12 further comprising operating the device in accordance with anticipatory behavior.

16. The method of claim 12 wherein bringing the value of said selected parameter closer to the determined target value causes a biological effect.

17. The method of claim 12 wherein the device has a plurality of influx and efflux ports which are operated to provide influx of the chemical of interest at one location on the device and efflux of the chemical of interest at another location on the device.

18. A method of operating a plurality of devices in a fluid environment where a chemical of interest has a rate of diffusion that is sufficiently low, with respect to chemical influx attainable by operating a selected device of the plurality, that operation of the selected device can materially affect concentrations of the chemical of interest in the fluid environment within one radius of the selected device, the method comprising the steps of:

determining an initial value of a selected parameter related to concentration of the chemical of interest, such parameter being selected from the group of concentration, flux, and a parameter that combines concentration and flux;

determining a diffusion coefficient of the chemical of interest in the fluid environment at the location of the selected device;

determining a target value for said selected parameter in the fluid environment at the location of the selected device; and directing the selected device to take at least one action to bring the value of said selected parameter closer to the determined target value in the fluid environment at the location of the selected device, said at least one action being selected from the group of:

changing the rate of influx of the selected device to change the concentration of the chemical of interest in the fluid environment at the location of the selected device;

moving to a location having a different concentration of the chemical of interest thereby allowing a different rate of absorption;

moving to a different location relative to another device in the plurality;

changing the orientation of the selected device to change the position of a selected port on the device to expose the selected port to fluid having a different concentration of the chemical of interest, thereby allowing a different rate of absorption; and changing the orientation of the selected device to change the position of at least one port with respect to another device in the plurality.

19. The method of claim 18 wherein said at least one action includes changing the orientation of the selected device to change the position with respect to the fluid environment of a selected port on the selected device.

20. The method of claim 18 wherein said at least one action includes moving the selected device to a location having a different concentration of the chemical of interest.

21. The method of claim 18 further comprising operating the selected device in accordance with anticipatory behavior.

22. The method of claim 18 wherein bringing the value of said selected parameter closer to the determined target value causes a biological effect.

23. The method of claim 18 wherein the selected device has a plurality of influx or efflux ports which are operated to provide influx of the chemical of interest at one location on the selected device and efflux of the chemical of interest at another location on the selected device.

24. The method of claim 18 where the selected device absorbs the chemical of interest while the same chemical is released into the fluid environment by at least one other device in the plurality.

* * * * *